United States Patent
Bonadio et al.

(10) Patent No.: US 9,700,296 B2
(45) Date of Patent: *Jul. 11, 2017

(54) WOUND RETRACTOR DEVICE

(71) Applicant: Atropos Limited, County Wicklow (IE)

(72) Inventors: Frank Bonadio, County Wicklow (IE); John Butler, County Mayo (IE); Trevor Vaugh, County Offaly (IE); Shane J. MacNally, County Wicklow (IE); Alan Reid, Dublin (IE)

(73) Assignee: Atropos Limited, County Wicklow (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/753,796

(22) Filed: Jun. 29, 2015

(65) Prior Publication Data

US 2016/0022257 A1 Jan. 28, 2016

Related U.S. Application Data

(63) Continuation of application No. 13/655,286, filed on Oct. 18, 2012, now Pat. No. 9,095,300, which is a
(Continued)

(30) Foreign Application Priority Data

Dec. 1, 1998  (IE) ......................................... 980997
Feb. 15, 1999 (IE) ......................................... 990111
(Continued)

(51) Int. Cl.
*A61B 1/32*  (2006.01)
*A61B 17/02* (2006.01)
(Continued)

(52) U.S. Cl.
CPC ............ *A61B 17/0293* (2013.01); *A61B 1/32* (2013.01); *A61B 17/3423* (2013.01);
(Continued)

(58) Field of Classification Search
CPC ............ A61B 17/3423; A61B 17/3431; A61B 17/0218; A61B 17/0469; A61B 17/0293
(Continued)

(56) References Cited

U.S. PATENT DOCUMENTS 1,157,202 A    10/1915 McLeland
1,598,284 A    8/1926  Kinney
(Continued)

FOREIGN PATENT DOCUMENTS

DE    37 39 532    12/1988
DE    37 37 121    5/1989
(Continued)

OTHER PUBLICATIONS

Kagaya, "Laparoscopic cholecystectomy via two ports, using the "Twin-Port" system", J. Hepatobiliary Pancreat Surg (2001) 8:76-80.

*Primary Examiner* — Anu Ramana
(74) *Attorney, Agent, or Firm* — Bookoff McAndrews, PLLC

(57) ABSTRACT

A wound protector and retractor device 1 comprises a sleeve 2, a distal member provided by a distal ring 3 of resilient material and a proximal member provided by a proximal ring 4. The sleeve 2 is led around the ring 3 and is free to move axially relative to the distal ring 3 somewhat in the manner of a pulley. The proximal ring 4 is fixed to the sleeve 2, in this case at the proximal inner end thereof. The sleeve 2 terminates in a handle or gripping portion which is reinforced by a gripping ring 15. The sleeve extends from the proximal ring 4 and the distal ring 3 is contained between inner and outer layers 2a, 2b of the sleeve 2. The resilient distal ring 3 is scrunched up and inserted through the incision 6. The sleeve 2 is then pulled upwardly. On pulling of the sleeve 2 upwardly the outer layer 2b is pulled up while the inner layer 2a is drawn around the proximal ring 3. This
(Continued)

results in shortening the axial extent between the proximal ring 4 and the distal ring 3, tensioning the sleeve and applying a retraction force to the margins of the incision 6. As the incision is being retracted the margins are also protected by the sleeve. On retraction, an access port is provided, for example for a surgeon to insert his hand and/or an instrument to perform a procedure. The device may be used as a retractor in open surgery or as a base for a valve/seal to allow it to be used in hand assisted laparoscopic surgery or for instrument access or hand access generally.

20 Claims, 52 Drawing Sheets

Related U.S. Application Data continuation of application No. 12/426,438, filed on Apr. 20, 2009, now Pat. No. 8,317,691, which is a continuation of application No. 10/678,653, filed on Oct. 6, 2003, now Pat. No. 7,559,893, which is a continuation-in-part of application No. 10/133,979, filed on Apr. 29, 2002, now Pat. No. 6,846,287, which is a continuation of application No. 09/801,826, filed on Mar. 9, 2001, now abandoned, which is a continuation of application No. PCT/IE99/00122, filed on Dec. 1, 1999, said application No. 10/678,653 is a continuation-in-part of application No. 10/374,523, filed on Feb. 27, 2003, now Pat. No. 7,445,597, which is a continuation of application No. 09/849,341, filed on May 7, 2001, now Pat. No. 6,582,364, which is a continuation of application No. 09/688,138, filed on Oct. 16, 2000, now Pat. No. 6,254,534.

(60) Provisional application No. 60/415,780, filed on Oct. 4, 2002, provisional application No. 60/428,215, filed on Nov. 22, 2002, provisional application No. 60/490,909, filed on Jul. 30, 2003.

(30) Foreign Application Priority Data

Oct. 14, 1999 (IE) .......................................... 990861
Dec. 16, 1999 (IE) .......................................... 991053
Feb. 18, 2000 (EP) .................................... 00650010

(51) Int. Cl.
*A61B 17/34* (2006.01)
*A61B 17/00* (2006.01)

(52) U.S. Cl.
CPC ...... *A61B 17/3498* (2013.01); *A61B 17/3431* (2013.01); *A61B 2017/00557* (2013.01); *A61B 2017/0212* (2013.01); *A61B 2017/0225* (2013.01); *A61B 2017/3443* (2013.01); *A61B 2017/3482* (2013.01); *A61B 2017/3484* (2013.01); *A61B 2017/3492* (2013.01)

(58) Field of Classification Search
USPC ......... 600/184, 201–208; 128/846, 849, 850, 128/852
See application file for complete search history.

(56) References Cited

U.S. PATENT DOCUMENTS

| | | |
|---|---|---|
| 1,810,466 A | 6/1931 | Deutsch |
| 2,219,564 A | 10/1940 | Reyniers |
| 2,305,289 A | 12/1942 | Coburg |
| 2,695,608 A | 11/1954 | Gibbon |
| 2,835,253 A | 5/1958 | Borgeson |
| 2,853,075 A | 10/1958 | Hoffman |
| 3,039,468 A | 6/1962 | Price |
| 3,111,943 A | 11/1963 | Orndorff |
| 3,244,169 A | 4/1966 | Baxter |
| 3,253,594 A | 5/1966 | Matthews et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,447,533 A | 6/1969 | Spicer |
| 3,522,800 A | 8/1970 | Lesser |
| 3,523,534 A | 8/1970 | Nolan |
| 3,570,475 A | 3/1971 | Weinstein |
| 3,592,198 A | 7/1971 | Evans |
| 3,656,485 A | 4/1972 | Robertson |
| 3,685,786 A | 8/1972 | Woodson |
| 3,717,151 A | 2/1973 | Collett |
| 3,729,006 A | 4/1973 | Wilder et al. |
| 3,782,370 A | 1/1974 | McDonald |
| 3,797,478 A | 3/1974 | Walsh et al. |
| 3,807,393 A | 4/1974 | McDonald |
| 3,828,764 A | 8/1974 | Jones |
| 3,841,332 A | 10/1974 | Treacle |
| 3,853,126 A | 12/1974 | Schulte |
| 3,853,127 A | 12/1974 | Spademan |
| 3,856,021 A | 12/1974 | Macintosh |
| 3,907,389 A | 9/1975 | Cox et al. |
| 3,915,171 A | 10/1975 | Shermeta |
| 3,965,890 A | 6/1976 | Gauthier |
| 3,996,623 A | 12/1976 | Kaster |
| 3,998,217 A | 12/1976 | Trumbull et al. |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,083,370 A | 4/1978 | Taylor |
| 4,096,853 A | 6/1978 | Weigand |
| 4,112,932 A | 9/1978 | Chiulli |
| 4,130,113 A | 12/1978 | Graham |
| 4,177,814 A | 12/1979 | Knepshield |
| 4,188,945 A | 2/1980 | Wenander |
| 4,217,664 A | 8/1980 | Faso |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lehrman |
| 4,367,728 A | 1/1983 | Mutke |
| 4,399,816 A | 8/1983 | Spangler |
| 4,411,659 A | 10/1983 | Jensen et al. |
| 4,421,296 A | 12/1983 | Stephens |
| 4,424,833 A | 1/1984 | Spector |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,485,490 A | 12/1984 | Akers et al. |
| 4,488,877 A | 12/1984 | Klein |
| 4,543,088 A | 9/1985 | Bootman |
| 4,550,713 A | 11/1985 | Hyman |
| 4,553,537 A | 11/1985 | Rosenberg |
| 4,601,710 A | 7/1986 | Moll |
| 4,610,665 A | 9/1986 | Matsumoto |
| 4,626,245 A | 12/1986 | Weinstein |
| 4,634,424 A | 1/1987 | O'Boyle |
| 4,649,904 A | 3/1987 | Krauter |
| 4,654,030 A | 3/1987 | Moll et al. |
| 4,673,393 A | 6/1987 | Suzuki et al. |
| 4,673,394 A | 6/1987 | Fenton |
| 4,755,170 A | 7/1988 | Golden |
| 4,776,843 A | 10/1988 | Martinez et al. |

(56) References Cited

U.S. PATENT DOCUMENTS

| | | |
|---|---|---|
| 4,777,943 A | 10/1988 | Chvapil |
| 4,784,646 A | 11/1988 | Feingold |
| 4,798,594 A | 1/1989 | Hillstead |
| 4,809,679 A | 3/1989 | Shimonaka |
| 4,863,438 A | 9/1989 | Gauderer |
| 4,889,107 A | 12/1989 | Kaufman |
| 4,895,565 A | 1/1990 | Hillstead |
| 4,897,081 A | 1/1990 | Poirier |
| 4,903,710 A | 2/1990 | Jessamine et al. |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,002,557 A | 3/1991 | Hasson |
| 5,015,228 A | 5/1991 | Columbus et al. |
| 5,019,101 A | 5/1991 | Purkait |
| 5,026,366 A | 6/1991 | Leckrone |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,074,878 A | 12/1991 | Bark et al. |
| 5,082,005 A | 1/1992 | Kaldany |
| 5,086,763 A | 2/1992 | Hathman |
| 5,092,846 A | 3/1992 | Nishijima |
| 5,125,897 A | 6/1992 | Quinn et al. |
| 5,129,885 A | 7/1992 | Green et al. |
| 5,141,498 A | 8/1992 | Christian |
| 5,149,327 A | 9/1992 | Oshiyama |
| 5,156,617 A | 10/1992 | Reid |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,178,162 A | 1/1993 | Bose |
| 5,188,595 A | 2/1993 | Jacobi |
| 5,192,301 A | 3/1993 | Kamiya et al. |
| 5,197,955 A | 3/1993 | Stephens et al. |
| 5,207,656 A | 5/1993 | Kranys |
| 5,209,737 A | 5/1993 | Ritchartt |
| 5,211,370 A | 5/1993 | Powers |
| 5,211,633 A | 5/1993 | Stouder |
| 5,213,114 A | 5/1993 | Bailey, Jr. |
| 5,234,455 A | 8/1993 | Mulhollan |
| 5,242,409 A | 9/1993 | Buelna |
| 5,248,304 A | 9/1993 | Vigdorchik et al. |
| 5,261,883 A | 11/1993 | Hood et al. |
| 5,263,922 A | 11/1993 | Sova et al. |
| 5,269,763 A | 12/1993 | Boehmer |
| 5,269,772 A | 12/1993 | Wilk |
| D343,236 S | 1/1994 | Quigley et al. |
| 5,279,575 A | 1/1994 | Sugarbaker |
| D346,022 S | 4/1994 | Quigley et al. |
| 5,299,582 A | 4/1994 | Potts |
| 5,300,036 A | 4/1994 | Mueller |
| 5,308,336 A | 5/1994 | Hart et al. |
| 5,309,896 A | 5/1994 | Moll et al. |
| 5,316,541 A | 5/1994 | Fischer |
| 5,320,611 A | 6/1994 | Bonutti |
| 5,330,437 A | 7/1994 | Durman |
| 5,330,497 A | 7/1994 | Freitas |
| 5,334,143 A | 8/1994 | Carroll |
| 5,336,192 A | 8/1994 | Palestrant |
| 5,342,315 A | 8/1994 | Rowe et al. |
| 5,342,385 A | 8/1994 | Norelli et al. |
| 5,350,364 A | 9/1994 | Stephens et al. |
| 5,364,345 A | 11/1994 | Lowery et al. |
| 5,366,478 A | 11/1994 | Brinkerhoff et al. |
| 5,368,545 A | 11/1994 | Schaller et al. |
| 5,383,861 A | 1/1995 | Hempel |
| 5,385,553 A | 1/1995 | Hart et al. |
| 5,391,153 A | 2/1995 | Haber et al. |
| 5,391,156 A | 2/1995 | Hildwein et al. |
| 5,395,367 A | 3/1995 | Wilk |
| 5,403,264 A | 4/1995 | Wohlers et al. |
| 5,407,433 A | 4/1995 | Loomas |
| 5,423,848 A | 6/1995 | Washizuka et al. |
| 5,429,609 A | 7/1995 | Yoon |
| 5,431,676 A | 7/1995 | Dubrul |
| 5,443,452 A | 8/1995 | Hart et al. |
| 5,456,284 A | 10/1995 | Ryan |
| 5,476,475 A | 12/1995 | Gadberry |
| 5,480,410 A | 1/1996 | Cuschieri et al. |
| 5,496,280 A | 3/1996 | Vandenbroek |
| 5,503,112 A | 4/1996 | Luhman |
| 5,514,109 A | 5/1996 | Mollenauer et al. |
| 5,514,133 A | 5/1996 | Golub et al. |
| 5,520,632 A | 5/1996 | Leveen |
| 5,522,791 A | 6/1996 | Leyva |
| 5,522,824 A | 6/1996 | Ashby |
| 5,524,644 A | 6/1996 | Crook |
| 5,526,536 A | 6/1996 | Cartmill |
| 5,545,179 A | 8/1996 | Williamson, IV |
| 5,562,632 A | 10/1996 | Davila |
| 5,562,688 A | 10/1996 | Riza |
| 5,577,993 A | 11/1996 | Zhu et al. |
| 5,582,577 A | 12/1996 | Lund et al. |
| 5,584,850 A | 12/1996 | Hart et al. |
| 5,601,579 A | 2/1997 | Semertzides |
| 5,620,415 A | 4/1997 | Lucey |
| 5,632,979 A | 5/1997 | Goldberg |
| 5,634,911 A | 6/1997 | Hermann et al. |
| 5,634,936 A | 6/1997 | Linden |
| 5,634,937 A | 6/1997 | Mollenauer et al. |
| 5,636,645 A | 6/1997 | Ou |
| 5,640,977 A | 6/1997 | Leahy et al. |
| 5,649,550 A | 7/1997 | Crook |
| 5,653,705 A | 8/1997 | de la Torre et al. |
| 5,657,963 A | 8/1997 | Hinchliffe |
| 5,658,272 A | 8/1997 | Hasson |
| 5,658,306 A | 8/1997 | Kieturakis |
| 5,672,168 A | 9/1997 | de la Torre et al. |
| 5,685,854 A | 11/1997 | Green |
| 5,707,703 A | 1/1998 | Rothrum et al. |
| 5,709,664 A | 1/1998 | Vandenbroek |
| 5,720,730 A | 2/1998 | Blake, III |
| 5,738,628 A | 4/1998 | Sierocuk et al. |
| 5,741,234 A | 4/1998 | Aboul-Hosn |
| 5,741,298 A | 4/1998 | MacLeod |
| 5,743,884 A | 4/1998 | Hasson et al. |
| 5,749,882 A | 5/1998 | Hart et al. |
| 5,755,660 A | 5/1998 | Tyagi |
| 5,769,783 A | 6/1998 | Fowler |
| 5,769,794 A | 6/1998 | Conlan et al. |
| 5,782,812 A | 7/1998 | Hart et al. |
| 5,795,290 A | 8/1998 | Bridges |
| 5,803,919 A | 9/1998 | Hart et al. |
| 5,803,921 A | 9/1998 | Bonadio |
| 5,807,350 A | 9/1998 | Diaz |
| 5,810,721 A | 9/1998 | Mueller et al. |
| 5,813,409 A | 9/1998 | Leahy et al. |
| 5,814,026 A | 9/1998 | Yoon |
| 5,817,062 A | 10/1998 | Flom |
| 5,820,555 A | 10/1998 | Mueller |
| 5,832,925 A | 11/1998 | Rothrum |
| 5,848,992 A | 12/1998 | Hart et al. |
| 5,853,395 A | 12/1998 | Crook et al. |
| 5,865,728 A | 2/1999 | Moll et al. |
| 5,871,474 A | 2/1999 | Hermann et al. |
| 5,882,344 A | 3/1999 | Stouder |
| 5,899,208 A | 5/1999 | Bonadio |
| 5,904,703 A | 5/1999 | Gilson |
| 5,906,577 A | 5/1999 | Beane et al. |
| 5,916,232 A | 6/1999 | Hart |
| 5,947,922 A | 9/1999 | MacLeod |
| 5,951,467 A | 9/1999 | Picha et al. |
| 5,957,913 A | 9/1999 | de la Torre et al. |
| 5,964,781 A | 10/1999 | Mollenauer et al. |
| 5,993,485 A | 11/1999 | Beckers |
| 5,994,450 A | 11/1999 | Pearce |
| 5,997,515 A | 12/1999 | de la Torre et al. |
| 6,024,736 A | 2/2000 | de la Torre et al. |
| 6,025,067 A | 2/2000 | Fay |

(56) References Cited

U.S. PATENT DOCUMENTS

| | | |
|---|---|---|
| 6,033,426 A | 3/2000 | Kaji |
| 6,033,428 A | 3/2000 | Sardella |
| 6,036,685 A | 3/2000 | Mueller |
| 6,042,573 A | 3/2000 | Lucey |
| 6,048,309 A | 4/2000 | Flom et al. |
| 6,059,816 A | 5/2000 | Moenning |
| 6,077,288 A | 6/2000 | Shimomura et al. |
| 6,099,506 A | 8/2000 | Macoviak et al. |
| 6,110,154 A | 8/2000 | Shimomura et al. |
| 6,123,689 A | 9/2000 | To |
| 6,142,935 A | 11/2000 | Flom et al. |
| 6,142,936 A | 11/2000 | Beane et al. |
| 6,149,642 A | 11/2000 | Gerhart et al. |
| 6,150,608 A | 11/2000 | Wambeke |
| 6,159,182 A | 12/2000 | Davis |
| 6,162,172 A | 12/2000 | Cosgrove et al. |
| 6,162,196 A | 12/2000 | Hart et al. |
| 6,162,206 A | 12/2000 | Bindokas |
| 6,163,949 A | 12/2000 | Neuenschwander |
| 6,164,279 A | 12/2000 | Tweedle |
| 6,171,282 B1 | 1/2001 | Ragsdale |
| 6,183,486 B1 | 2/2001 | Snow et al. |
| 6,238,373 B1 | 5/2001 | de la Torre et al. |
| 6,254,533 B1 | 7/2001 | Fadem et al. |
| 6,254,534 B1 | 7/2001 | Butler et al. |
| 6,258,065 B1 | 7/2001 | Dennis |
| 6,315,770 B1 | 11/2001 | de la Torre et al. |
| 6,319,246 B1 | 11/2001 | de la Torre et al. |
| 6,322,541 B2 | 11/2001 | West |
| 6,328,730 B1 | 12/2001 | Harkrider, Jr. |
| 6,346,074 B1 | 2/2002 | Roth |
| 6,382,211 B1 | 5/2002 | Crook |
| 6,420,475 B1 | 7/2002 | Chen |
| 6,440,063 B1 | 8/2002 | Beane |
| 6,450,983 B1 | 9/2002 | Rambo |
| 6,454,783 B1 | 9/2002 | Piskun |
| 6,464,686 B1 | 10/2002 | O'Hara et al. |
| 6,485,435 B1 | 11/2002 | Bakal |
| 6,485,467 B1 | 11/2002 | Crook et al. |
| 6,488,620 B1 | 12/2002 | Segermark et al. |
| 6,533,734 B1 | 3/2003 | Corley, III et al. |
| 6,551,270 B1 | 4/2003 | Bimbo et al. |
| 6,554,793 B1 | 4/2003 | Pauker |
| 6,569,119 B1 | 5/2003 | Haberland et al. |
| 6,578,577 B2 | 6/2003 | Bonadio et al. |
| 6,582,364 B2 | 6/2003 | Butler et al. |
| 6,589,167 B1 | 7/2003 | Shimomura |
| 6,589,211 B1 | 7/2003 | MacLeod |
| 6,607,504 B2 | 8/2003 | Haarala |
| 6,613,952 B2 | 9/2003 | Rambo |
| 6,623,426 B2 | 9/2003 | Bonadio et al. |
| 6,706,050 B1 | 3/2004 | Giannadakis |
| 6,714,298 B2 | 3/2004 | Ryer |
| 6,723,044 B2 | 4/2004 | Pulford |
| 6,793,621 B2 | 9/2004 | Butler et al. |
| 6,796,940 B2 | 9/2004 | Bonadio et al. |
| 6,797,765 B2 | 9/2004 | Pearce |
| 6,814,078 B2 | 11/2004 | Crook |
| 6,814,700 B1 | 11/2004 | Mueller et al. |
| 6,840,951 B2 | 1/2005 | de la Torre et al. |
| 6,846,287 B2 | 1/2005 | Bonadio et al. |
| 6,860,463 B2 | 3/2005 | Hartley |
| 6,866,861 B1 | 3/2005 | Luhman |
| 6,884,253 B1 | 4/2005 | McFarlane |
| 6,902,541 B2 | 6/2005 | McNally et al. |
| 6,908,430 B2 | 6/2005 | Caldwell |
| 6,916,331 B2 | 7/2005 | Mollenauer et al. |
| 6,936,037 B2 | 8/2005 | Bubb |
| 6,939,296 B2 | 9/2005 | Ewers |
| 6,945,932 B1 | 9/2005 | Caldwell et al. |
| 6,958,037 B2 | 10/2005 | Ewers |
| 6,979,324 B2 | 12/2005 | Byordi |
| 7,008,377 B2 | 3/2006 | Beane |
| 7,052,454 B2 | 5/2006 | Taylor |
| 7,081,089 B2 | 7/2006 | Bonadio et al. |
| 7,083,626 B2 | 8/2006 | Hart et al. |
| 7,112,185 B2 | 9/2006 | Hart et al. |
| 7,118,528 B1 | 10/2006 | Piskun |
| 7,153,319 B1 | 12/2006 | Haberland et al. |
| 7,195,590 B2 | 3/2007 | Butler et al. |
| 7,297,106 B2 | 11/2007 | Yamada et al. |
| 7,300,399 B2 | 11/2007 | Bonadio et al. |
| 7,344,547 B2 | 3/2008 | Piskun |
| 7,445,597 B2 | 11/2008 | Butler et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,749,415 B2 | 7/2010 | Brustad et al. |
| 7,753,901 B2 | 7/2010 | Piskun et al. |
| 7,837,612 B2 | 11/2010 | Gill et al. |
| 7,867,164 B2 | 1/2011 | Butler et al. |
| 7,909,760 B2 | 3/2011 | Albrecht et al. |
| 7,998,068 B2 | 8/2011 | Bonadio et al. |
| 8,012,088 B2 | 9/2011 | Butler et al. |
| 8,021,296 B2 | 9/2011 | Bonadio et al. |
| 8,157,817 B2 | 4/2012 | Bonadio et al. |
| 8,187,178 B2 | 5/2012 | Bonadio et al. |
| 8,317,691 B2 | 11/2012 | Bonadio et al. |
| 8,343,047 B2 | 1/2013 | Albrecht et al. |
| 8,375,955 B2 | 2/2013 | Desai et al. |
| 8,485,970 B2 | 7/2013 | Widenhouse et al. |
| 8,518,024 B2 | 8/2013 | Williams et al. |
| 8,657,740 B2 | 2/2014 | Bonadio et al. |
| 8,734,336 B2 | 5/2014 | Bonadio et al. |
| 8,740,785 B2 | 6/2014 | Butler et al. |
| 8,752,553 B2 | 6/2014 | Bonadio et al. |
| 8,876,708 B1 | 11/2014 | Piskun et al. |
| 8,888,693 B2 | 11/2014 | Bonadio et al. |
| 8,961,406 B2 | 2/2015 | Ortiz et al. |
| 8,961,407 B2 | 2/2015 | Piskun et al. |
| 8,986,202 B2 | 3/2015 | Butler et al. |
| 9,078,695 B2 | 7/2015 | Hess et al. |
| 9,095,300 B2 | 8/2015 | Bonadio et al. |
| 9,131,835 B2 | 9/2015 | Widenhouse et al. |
| 9,271,753 B2 | 3/2016 | Butler et al. |
| 9,277,908 B2 | 3/2016 | Butler et al. |
| 2001/0037053 A1 | 11/2001 | Bonadio et al. |
| 2001/0039430 A1 | 11/2001 | Dubrul et al. |
| 2001/0047188 A1 | 11/2001 | Bonadio et al. |
| 2002/0002324 A1 | 1/2002 | Mcmanus |
| 2002/0010389 A1 | 1/2002 | Butler et al. |
| 2002/0038077 A1 | 3/2002 | de la Torre et al. |
| 2002/0072762 A1 | 6/2002 | Bonadio et al. |
| 2002/0111536 A1 | 8/2002 | Cuschieri et al. |
| 2003/0028179 A1 | 2/2003 | Piskun |
| 2003/0078478 A1 | 4/2003 | Bonadio et al. |
| 2003/0139756 A1 | 7/2003 | Brustad |
| 2003/0187376 A1 | 10/2003 | Rambo |
| 2003/0192553 A1 | 10/2003 | Rambo |
| 2003/0225392 A1 | 12/2003 | McMichael |
| 2003/0236549 A1 | 12/2003 | Bonadio et al. |
| 2004/0015185 A1 | 1/2004 | Ewers et al. |
| 2004/0024363 A1 | 2/2004 | Goldberg |
| 2004/0049099 A1 | 3/2004 | Ewers et al. |
| 2004/0049100 A1 | 3/2004 | Butler |
| 2004/0068232 A1 | 4/2004 | Hart et al. |
| 2004/0073090 A1 | 4/2004 | Butler |
| 2004/0092795 A1 | 5/2004 | Bonadio et al. |
| 2004/0092796 A1 | 5/2004 | Butler et al. |
| 2004/0093018 A1 | 5/2004 | Johnson |
| 2004/0097793 A1 | 5/2004 | Butler et al. |
| 2004/0106942 A1 | 6/2004 | Taylor |
| 2004/0143158 A1 | 7/2004 | Hart et al. |
| 2004/0154624 A1 | 8/2004 | Bonadio et al. |
| 2004/0215063 A1 | 10/2004 | Bonadio et al. |
| 2004/0230161 A1 | 11/2004 | Zeiner |
| 2004/0249248 A1 | 12/2004 | Bonadio et al. |
| 2004/0260244 A1 | 12/2004 | Piechowicz et al. |
| 2005/0020884 A1 | 1/2005 | Heart et al. |
| 2005/0033246 A1 | 2/2005 | Ahlberg |
| 2005/0059865 A1 | 3/2005 | Kahle |
| 2005/0065475 A1 | 3/2005 | Hart et al. |
| 2005/0065543 A1 | 3/2005 | Kahle |
| 2005/0090713 A1 | 4/2005 | Gonzales |

(56) References Cited

U.S. PATENT DOCUMENTS

| | | |
|---|---|---|
| 2005/0090716 A1 | 4/2005 | Bonadio et al. |
| 2005/0090717 A1 | 4/2005 | Bonadio et al. |
| 2005/0131349 A1 | 6/2005 | Albrecht |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0159647 A1 | 7/2005 | Hart et al. |
| 2005/0192483 A1 | 9/2005 | Bonadio et al. |
| 2005/0192598 A1 | 9/2005 | Johnson |
| 2005/0197537 A1 | 9/2005 | Bonadio et al. |
| 2005/0203346 A1 | 9/2005 | Bonadio et al. |
| 2005/0209510 A1 | 9/2005 | Bonadio et al. |
| 2005/0222582 A1 | 10/2005 | Wenchell |
| 2005/0240082 A1 | 10/2005 | Bonadio et al. |
| 2005/0241647 A1 | 11/2005 | Nguyen |
| 2005/0267419 A1 | 12/2005 | Smith |
| 2005/0277946 A1 | 12/2005 | Greenhalgh |
| 2005/0288558 A1 | 12/2005 | Ewers |
| 2005/0288634 A1 | 12/2005 | O'Herron |
| 2006/0020164 A1 | 1/2006 | Butler et al. |
| 2006/0020241 A1 | 1/2006 | Piskun et al. |
| 2006/0030755 A1 | 2/2006 | Ewers et al. |
| 2006/0041270 A1 | 2/2006 | Lenker |
| 2006/0047284 A1 | 3/2006 | Gresham |
| 2006/0047293 A1 | 3/2006 | Haberland et al. |
| 2006/0106402 A1 | 5/2006 | McLucas |
| 2006/0149137 A1 | 7/2006 | Pingleton et al. |
| 2006/0149306 A1 | 7/2006 | Hart et al. |
| 2006/0161050 A1 | 7/2006 | Butler et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0258899 A1 | 11/2006 | Gill et al. |
| 2006/0264706 A1 | 11/2006 | Piskun |
| 2007/0004968 A1 | 1/2007 | Bonadio et al. |
| 2007/0049966 A1 | 3/2007 | Bonadio et al. |
| 2007/0093695 A1 | 4/2007 | Bonadio et al. |
| 2007/0118175 A1 | 5/2007 | Butler et al. |
| 2007/0185387 A1 | 8/2007 | Albrecht et al. |
| 2007/0203398 A1 | 8/2007 | Bonadio et al. |
| 2007/0255219 A1 | 11/2007 | Vaugh et al. |
| 2007/0287889 A1 | 12/2007 | Mohr |
| 2007/0299387 A1 | 12/2007 | Williams et al. |
| 2008/0027476 A1 | 1/2008 | Piskun |
| 2008/0097162 A1 | 4/2008 | Bonadio et al. |
| 2008/0097163 A1 | 4/2008 | Butler et al. |
| 2008/0255519 A1 | 10/2008 | Piskun et al. |
| 2008/0281161 A1 | 11/2008 | Albrecht et al. |
| 2008/0281162 A1 | 11/2008 | Albrecht et al. |
| 2009/0012477 A1 | 1/2009 | Norton et al. |
| 2009/0036745 A1 | 2/2009 | Bonadio et al. |
| 2009/0069837 A1 | 3/2009 | Bonadio et al. |
| 2009/0093683 A1 | 4/2009 | Richard et al. |
| 2009/0149714 A1 | 6/2009 | Bonadio |
| 2009/0187079 A1 | 7/2009 | Albrecht et al. |
| 2009/0221966 A1 | 9/2009 | Richard |
| 2009/0292176 A1 | 11/2009 | Bonadio et al. |
| 2009/0326330 A1 | 12/2009 | Bonadio et al. |
| 2010/0057121 A1 | 3/2010 | Piskun et al. |
| 2010/0063362 A1 | 3/2010 | Bonadio et al. |
| 2010/0063364 A1 | 3/2010 | Bonadio et al. |
| 2010/0081880 A1 | 4/2010 | Widenhouse et al. |
| 2010/0081881 A1 | 4/2010 | Murray et al. |
| 2010/0113886 A1 | 5/2010 | Piskun et al. |
| 2010/0204548 A1 | 8/2010 | Bonadio et al. |
| 2010/0217087 A1 | 8/2010 | Bonadio et al. |
| 2010/0261972 A1 | 10/2010 | Widenhouse et al. |
| 2010/0274091 A1 | 10/2010 | Rothstein et al. |
| 2010/0274093 A1 | 10/2010 | Shelton, IV |
| 2010/0280326 A1 | 11/2010 | Hess et al. |
| 2011/0011410 A1 | 1/2011 | Desai et al. |
| 2011/0071359 A1 | 3/2011 | Bonadio et al. |
| 2011/0092778 A1 | 4/2011 | Butler et al. |
| 2011/0270195 A1 | 11/2011 | Piskun |
| 2012/0016394 A1 | 1/2012 | Bonadio et al. |
| 2012/0022333 A1 | 1/2012 | Main et al. |
| 2012/0029297 A1 | 2/2012 | Bonadio et al. |
| 2012/0116172 A1 | 5/2012 | Butler et al. |
| 2012/0123214 A1 | 5/2012 | Bonadio et al. |
| 2013/0041231 A1 | 2/2013 | Bonadio et al. |
| 2013/0060093 A1 | 3/2013 | Bonadio et al. |
| 2013/0116509 A1 | 5/2013 | Bonadio et al. |
| 2013/0245373 A1 | 9/2013 | Okoniewski |
| 2014/0107425 A1 | 4/2014 | Bonadio et al. |
| 2014/0303443 A1 | 10/2014 | Bonadio et al. |
| 2014/0323809 A1 | 10/2014 | Bonadio et al. |
| 2015/0148611 A1 | 5/2015 | Bonadio et al. |
| 2015/0272563 A1 | 10/2015 | Butler et al. |
| 2015/0335353 A1 | 11/2015 | Widenhouse et al. |
| 2016/0022257 A1 | 1/2016 | Bonadio et al. |

FOREIGN PATENT DOCUMENTS

| | | |
|---|---|---|
| DE | 296 00 939 | 6/1998 |
| EP | 0113520 | 7/1984 |
| EP | 0142262 | 5/1985 |
| EP | 0537768 | 4/1993 |
| EP | 0950376 | 10/1999 |
| EP | 1118657 | 7/2001 |
| EP | 1312318 | 5/2003 |
| EP | 1593348 | 11/2005 |
| EP | 2168511 | 3/2010 |
| FR | 1456623 | 9/1966 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1496696 | 12/1977 |
| GB | 2071502 | 9/1981 |
| GB | 2255019 | 10/1992 |
| GB | 2275420 | 8/1994 |
| JP | 10-108868 | 4/1998 |
| JP | 11-290327 | 10/1999 |
| JP | 2001-61850 | 3/2001 |
| JP | 2002-28163 | 1/2002 |
| JP | 2004-509659 | 4/2004 |
| JP | 2004-195037 | 7/2004 |
| JP | 2011-98138 | 5/2011 |
| SU | 1342485 | 1/1997 |
| WO | WO 86/06272 | 11/1986 |
| WO | WO 92/11880 | 7/1992 |
| WO | WO 92/21292 | 12/1992 |
| WO | WO 93/05740 | 4/1993 |
| WO | WO 95/05207 | 2/1995 |
| WO | WO 95/07056 | 3/1995 |
| WO | WO 95/22289 | 8/1995 |
| WO | WO 95/24864 | 9/1995 |
| WO | WO 95/27445 | 10/1995 |
| WO | WO 95/27468 | 10/1995 |
| WO | WO 96/36283 | 11/1996 |
| WO | WO 97/32514 | 9/1997 |
| WO | WO 97/32515 | 9/1997 |
| WO | WO 98/35614 | 8/1998 |
| WO | WO 98/48724 | 11/1998 |
| WO | WO 99/03416 | 1/1999 |
| WO | WO 99/25268 | 5/1999 |
| WO | WO 99/29250 | 6/1999 |
| WO | WO 00/32116 | 6/2000 |
| WO | WO 00/32117 | 6/2000 |
| WO | WO 00/32119 | 6/2000 |
| WO | WO 00/32120 | 6/2000 |
| WO | WO 00/35356 | 6/2000 |
| WO | WO 00/54675 | 9/2000 |
| WO | WO 00/54676 | 9/2000 |
| WO | WO 00/54677 | 9/2000 |
| WO | WO 01/08563 | 2/2001 |
| WO | WO 01/08581 | 2/2001 |
| WO | WO 01/26558 | 4/2001 |
| WO | WO 01/91652 | 12/2001 |
| WO | WO 01/91653 | 12/2001 |

(56) References Cited

FOREIGN PATENT DOCUMENTS

| | | |
|---|---|---|
| WO | WO 02/17800 A2 | 3/2002 |
| WO | WO 02/34108 A2 | 5/2002 |
| WO | WO 03/026512 A1 | 4/2003 |
| WO | WO 03/034908 A3 | 5/2003 |
| WO | WO 03/061480 A1 | 7/2003 |
| WO | WO 03/103548 A1 | 12/2003 |
| WO | WO 2004/026153 A1 | 4/2004 |
| WO | WO 2004/030547 A1 | 4/2004 |
| WO | WO 2005/009257 A2 | 2/2005 |
| WO | WO 2005/034766 A2 | 4/2005 |
| WO | WO 2005/089661 | 9/2005 |
| WO | WO 2006/040748 A1 | 4/2006 |
| WO | WO 2006/059318 | 8/2006 |
| WO | WO 2008/121294 A1 | 10/2008 |
| WO | WO 2009/035663 A2 | 3/2009 |
| WO | WO 2014/144233 A1 | 9/2014 |

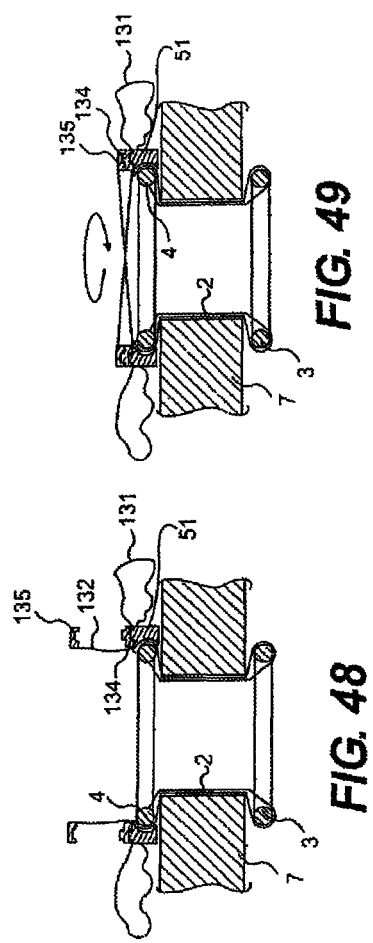

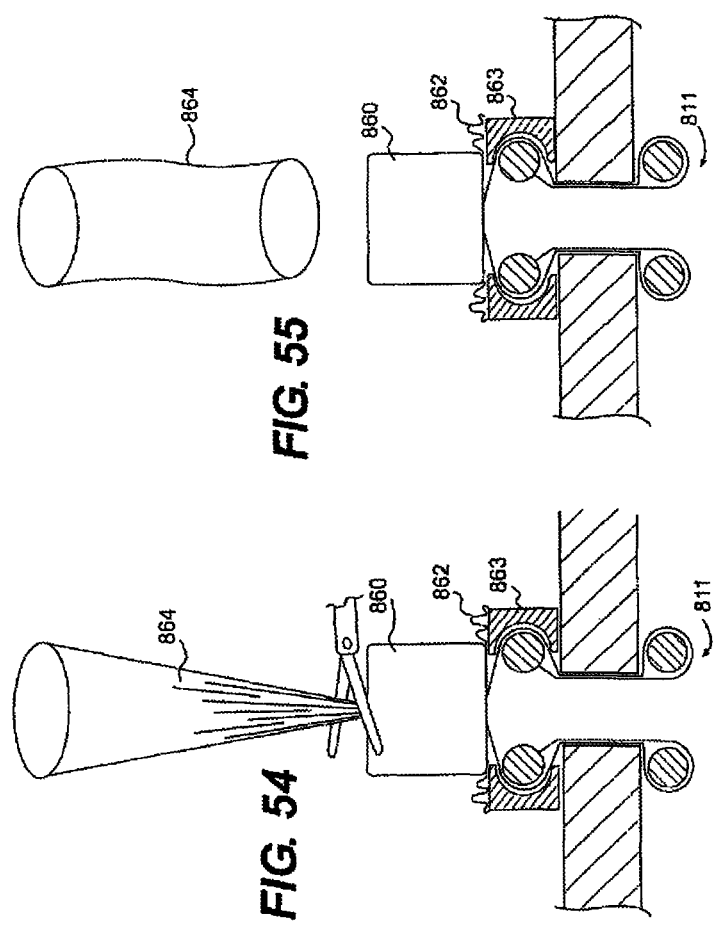

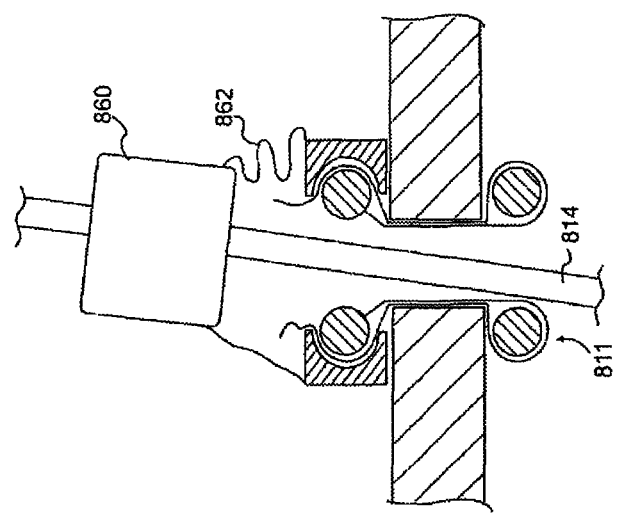
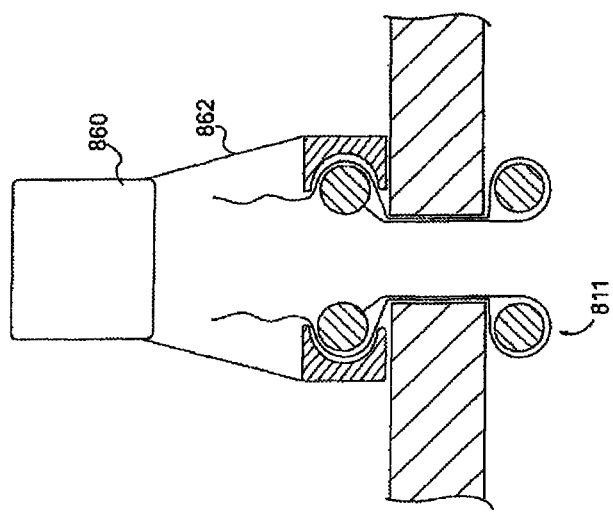

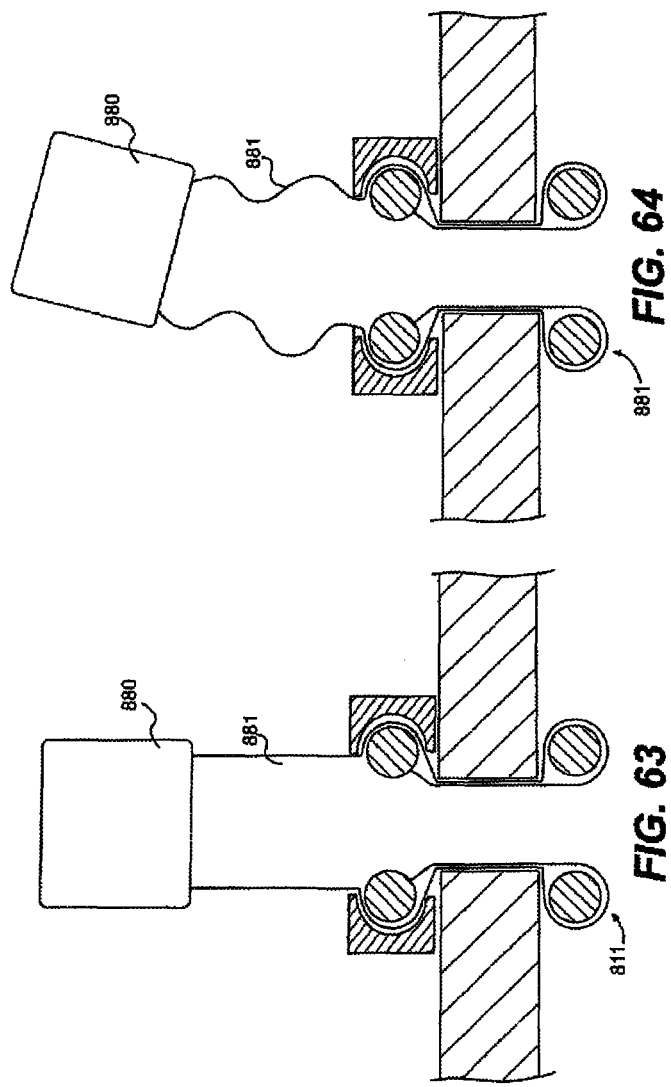

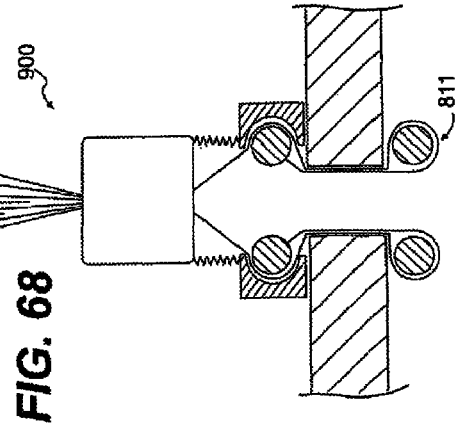
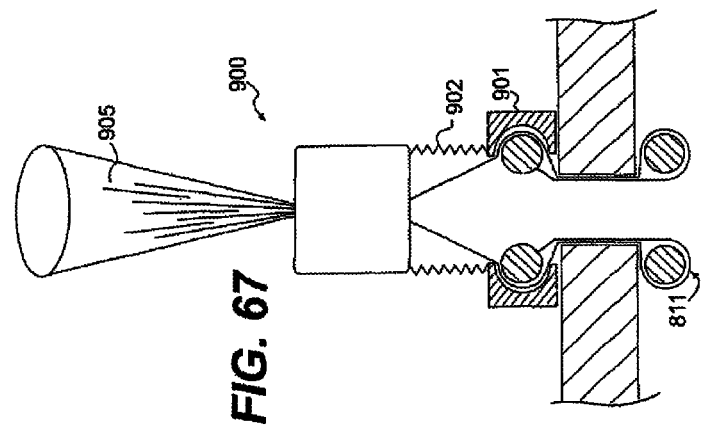

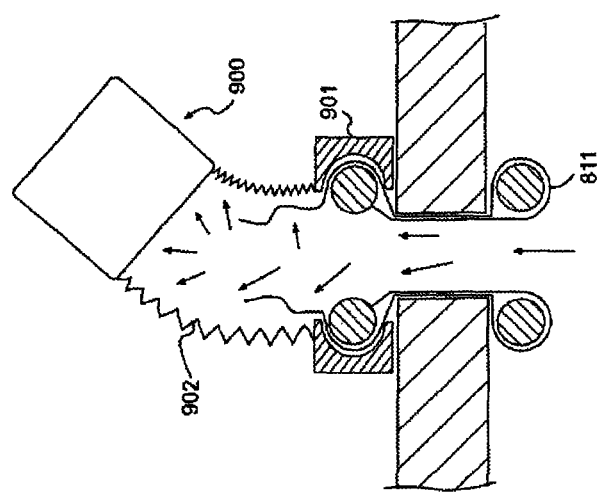
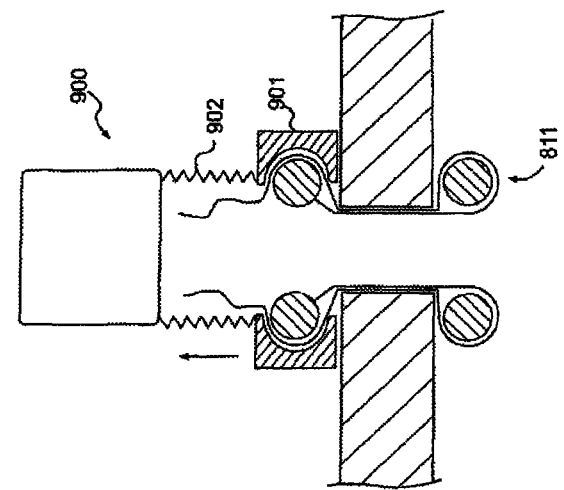

WOUND RETRACTOR DEVICE

This application is a Continuation of U.S. application Ser. No. 13/655,286, filed Oct. 18, 2012, which is a Continuation of U.S. application Ser. No. 12/426,438, filed Apr. 20, 2009, now U.S. Pat. No. 8,317,691, which is a Continuation of U.S. application Ser. No. 10/678,653, filed Oct. 6, 2003, now U.S. Pat. No. 7,559,893, which is a Continuation-In-Part of U.S. application Ser. No. 10/133,979, filed Apr. 29, 2002, now U.S. Pat. No. 6,846,287, which is a Continuation of U.S. application Ser. No. 09/801,826, filed Mar. 9, 2001, now abandoned, which is a Continuation of International Application No. PCT/IE99/0022, filed Dec. 1, 1999.

U.S. application Ser. No. 10/678,653 is also a Continuation-In-Part of U.S. application Ser. No. 10/374,523, filed Feb. 27, 2003, now U.S. Pat. No. 7,445,597, which is a Continuation of U.S. application Ser. No. 09/849,341, filed May 7, 2001, now U.S. Pat. No. 6,582,364, which is a Continuation of U.S. application Ser. No. 09/688,138, filed Oct. 16, 2000, now. U.S. Pat. No. 6,254,534.

U.S. application Ser. No. 10/678,653 also claims benefits of priority of U.S. Provisional Application No. 60/415,780, filed Oct. 4, 2002, 60/428,215, filed Nov. 22, 2002, and U.S. Provisional Application No. 60/490,909, filed Jul. 30, 2003.

U.S. application Ser. No. 09/688,138 also claims the benefits of priority of European Application No. 00650010, filed Feb. 18, 2000, Application No. 991053, filed Dec. 16, 1999, in Ireland, Application No. 990861, filed Oct. 14, 1999, in Ireland.

International Application No. PCT/IE99/0022 also claims the benefits of priority of Application No. 990111, filed Feb. 15, 1999, in Ireland, and Application No. 980997, filed Dec. 1, 1998, in Ireland.

All of the above-listed applications are incorporated herein by reference in their entireties.

INTRODUCTION

The invention relates to a retractor. In particular the invention relates to a retractor for retracting the margins of an incision or a natural bodily orifice to provide maximum exposure of an organ or body structures for examination and/or access for surgical procedures, while also providing protection for the exposed sides of the incised tissue.

Various retractors are known. Some known retractors are difficult and cumbersome to use, and/or are relatively expensive. In addition, some known retractors are limited to use with a particular size of incision and a particular patient anatomy.

This invention is directed towards providing an improved wound retractor which will overcome at least some of these problems, and in addition provide a means of wound protection during a surgical procedure.

STATEMENTS OF INVENTION

According to the invention there is provided a wound protector and retractor device comprising:
   a longitudinal axis;
   a distal member;
   a proximal member; and
   a sleeve extending at least between the distal member and the proximal member,
   the sleeve having a proximal gripping portion for pulling the sleeve upwardly to shorten an axial extent located between the distal member and the proximal member.

In the device, on release of the gripping portion the shortened axial extent between the distal member and the proximal member is substantially maintained without a requirement for an additional locking device.

In one embodiment the proximal gripping portion is provided at a proximal end portion of the sleeve. The gripping portion may be reinforced by a reinforcing arrangement such as a gripping ring. The gripping ring may be mounted to the sleeve.

In one embodiment the sleeve is fixed to the proximal member at a first end portion and is movable over the proximal member at a second end portion. The sleeve may be axially slidable over the proximal member at the second end portion.

In another embodiment the second end portion of the sleeve is slidingly received over a portion of the proximal member to allow relative movement between the sleeve and the proximal member to shorten the axial extent of the sleeve located between the distal member and the proximal member. The portion of the proximal member that slidingly receives the sleeve may include an outer portion of the proximal member. The second end portion of the sleeve may be biased against the proximal member.

In one embodiment the proximal member is located within the sleeve.

The proximal member may form a part of a securing arrangement configured to substantially fix the axial extent of the sleeve located between the distal member and the proximal member at a desired length.

The sleeve may extend from the proximal member, around the distal member, and has a return section outside of the proximal member, the return section providing the proximal gripping portion.

In one embodiment the distal member comprises a distal ring which may be an O-ring.

The distal ring may be formed of an elastomeric material.

In one embodiment the proximal member comprises a proximal ring which may be an O-ring.

The proximal ring may be relatively rigid with respect to the distal ring.

In one embodiment the sleeve is of a pliable material.

The wound protector and retractor device may comprise a guide member for a proximal portion of the sleeve.

The sleeve may extend between the guide member and the proximal member.

The guide member may comprise a receiver for the proximal member. For example, the guide member may have an inwardly facing recess defining a receiver for the proximal member. In one case the proximal member comprises a proximal ring and the recess has a shape which is complementary to that of the proximal ring, for example the recess may be substantially C-shaped in transverse cross section.

In another embodiment a lock may be provided for locking the guide member to the proximal member. The guide member may be engagable with the proximal member to provide the lock.

In some cases the guide member may be an interference fit with the proximal member.

In one embodiment, on retraction of an incision the sleeve defines an excess sleeve portion extending between the proximal member and the gripping portion.

The excess sleeve portion may be removed. Alternatively the excess sleeve portion is inserted through the retractor and in this case may define an organ retainer.

Alternatively the excess sleeve portion is configured to form a seal such as a forearm seal or an instrument seal.

The seal may comprise an iris valve.

In one embodiment the device comprises a guide member for a proximal portion of the sleeve and the excess sleeve material is mounted to the guide member. The excess sleeve material together with the guide member may define a chamber. The chamber may have an inflation port. In one case, on inflation, the chamber defines a seal for an object such as a surgeon's forearm or an instrument shaft.

In one embodiment the device comprises a first proximal mounting member and a second proximal mounting member between which at least portion of a sleeve extends. The first and second mounting members may be movable relative to one another.

The mounting members may be movable axially relative to one another and/or the mounting members are rotationally movable relative to one another.

In one arrangement the mounting members are movable relative to one another to configure at least portion of the proximal portion of the sleeve to form a seal. The mounting members may be movable to twist the sleeve to form an iris.

In one embodiment the device comprises a biassing member for biassing the seal into a desired configuration such as a closed configuration.

The biassing member may be a spring such as a coil spring.

In one embodiment the device further comprises a lock for locking the first and second mounting members together. The second mounting member may be engagable with the first mounting member to provide the lock. The lock may be provided by snap fitting engagement between the mounting members. Alternatively one mounting member is an interference fit with the other mounting member to provide the lock.

In one case the sleeve which extends between the mounting members is a proximal portion of the retracting sleeve.

In another case the sleeve which extends between the mounting members is a connecting sleeve which is separate from the retracting sleeve.

The first mounting member may comprise a ring member.

The second mounting member may comprise a ring member.

In one embodiment the wound protector and retractor device further includes a valve.

The valve may be attached to the retractor device.

In one case the valve is attached to the proximal portion of the sleeve.

In another case a connector is provided between the device and the valve. The connector may comprise a connector sleeve. The connector sleeve may be of substantially fixed length.

In one embodiment a flexible joint is provided between the valve and the device.

In another embodiment a malleable joint is provided between the valve and the device. In this case the valve may be offset with respect to the longitudinal axis of the wound retractor.

In one embodiment the malleable joint is provided by a malleable connecting sleeve section. The malleable connecting sleeve section may be of corrugated configuration.

In one embodiment the valve is a lip seal.

Alternatively the valve is an iris seal.

The valve may be a forearm seal or an instrument seal.

In one embodiment the device comprises a release arrangement for releasing the device from a retracting configuration. The release arrangement may comprise a pulling device. The pulling device may be coupled to the distal member. The pulling device may comprise a pull cord or a ribbon.

In another aspect the invention provides a wound protector and retractor device comprising:
  a longitudinal axis;
  a distal member;
  a proximal member; and
  a sleeve extending at least between the distal member and the proximal member,
    the sleeve, on retraction of an incision, defining an excess sleeve portion extending proximally from the proximal member.

In one embodiment the excess sleeve portion is configured to form a seal such as a forearm seal or an instrument seal. The seal may comprise an iris valve.

In a further aspect the invention provides a wound protector and retractor device comprising:
  a longitudinal axis;
  a distal member;
  a proximal member; and
  a sleeve extending at least between the distal member and the proximal member,
    the device further comprising a first proximal mounting member and a second proximal mounting member between which at least portion of a sleeve extends.

The first and second mounting members may be movable relative to one another. The mounting members may be movable axially relative to one another and/or the mounting members are rotationally movable relative to one another. In one case the mounting members are movable relative to one another to configure at least portion of the proximal portion of the sleeve to form a seal. The mounting members may be movable to twist the sleeve to form an iris. The device may comprise a biassing member for biassing the seal into a desired configuration such as a closed configuration.

In another aspect the invention provides a surgical device comprising a wound retractor, a valve and a connector between the wound protector and the valve, the wound retractor comprising:
  a longitudinal axis;
  a distal member;
  a proximal member; and
  a sleeve extending at least between the distal member and the proximal member.

The connector may comprise a connector sleeve which may be of substantially fixed length. The connector may comprise a flexible joint between the valve and the retractor. Alternatively the connector comprises a malleable joint between the valve and the retractor. The valve may be offset with respect to the longitudinal axis of the wound retractor. The malleable joint is provided by a malleable connecting sleeve section. The malleable connecting sleeve sections may be of corrugated configuration.

In another aspect the invention provides a method for retracting an incision comprising the steps of:
  making an incision in a patient;
  providing a wound retractor comprising a longitudinal axis, a distal member, a proximal member, and a sleeve extending at least between the distal member and the proximal member, the sleeve having a proximal gripping portion;
  inserting the distal member through the incision such that the sleeve extends through the incision and the proximal member is located outside of the incision;

gripping the gripping portion of the sleeve and pulling the sleeve upwardly to shorten an axial extent of the sleeve located between the distal member and the proximal member.

In one embodiment, on release of the gripping portion the shortened axial extent of the sleeve between the distal member and the proximal member is substantially maintained.

The sleeve may be fixed to the proximal member at a first end portion and extending over the proximal member at a second end portion, and the method comprises moving the sleeve over the proximal member as the sleeve is pulled upwardly to shorten the axial extent of the sleeve located between the distal member and the proximal member. The method may comprise the step of moving the sleeve relative to the proximal member including sliding a portion of the sleeve against a radially outer portion of the proximal member.

In one embodiment a portion of the sleeve located between the distal member and the proximal member includes two material layers. The sleeve may be wrapped around the distal member to form the two material layers.

The method may comprise sealing the wound retractor, for example by attaching a seal to the wound retractor, by releaseably mounting a seal to the wound retractor. A seal may be mounted a proximal end of the wound retractor. A seal may be mounted to a proximal end of the sleeve.

In one case the retractor comprises a mounting member and the seal is attached to the mounting member.

In one embodiment the seal is attached to the proximal end of the wound retractor using a connector.

The connector may be a connecting sleeve. The connector may be at least partially of a flexible material. Alternatively the connector is at least partially of a malleable material and the method may comprise the step of manipulating the connector into a desired configuration. In one case the desired configuration is a configuration in which the seal is offset from the longitudinal axis of the wound retractor.

In one embodiment the method comprises pulling the sleeve upwardly to provide an excess sleeve portion extending proximally of the wound retractor. In one case the method comprises the step of cutting away the excess sleeve portion. In another case the method comprises the step of inserting the excess sleeve portion through the retractor. The excess sleeve material may be inserted through the retractor providing an organ retainer.

In another case the method comprises the step of manipulating the excess sleeve portion to provide a seal.

In one embodiment the retractor comprises a proximal mounting member and the excess sleeve portion is attached to the mounting member.

In another embodiment the excess sleeve portion forms, with the mounting member, a chamber. The chamber may have an inflation port and the method comprises inflating the chamber to provide a seal.

The seal may be a lip seal or an iris seal.

In one embodiment the wound retractor is sealed with a forearm seal.

In another embodiment the wound retractor is sealed with an instrument seal.

In one case the incision is of a size to receive an instrument, when retracted.

In another case the incision is of a size to receive a forearm, when retracted.

In a further case the incision is of a size to provide a site for open surgery, when retracted.

According to the invention there is provided a medical device comprising:
 a retractor member comprising a distal portion for insertion through an incision made in a patient, and a proximal portion for extending from the incision and outside of the patient;
 a distal member associated with the distal portion of the retractor member;
 a proximal member associated with the proximal portion of the retractor member;
 the retractor member being axially movable relative to the distal member to draw the proximal and distal members towards one another thereby shortening the axial extent of the retractor member between the proximal and distal members.

In one embodiment the retractor member comprises a sleeve member. The sleeve member preferably extends around the distal member.

In one embodiment the distal member is a ring member such as a resilient ring member, for example, an O-ring.

In one embodiment the proximal member is connected to the retractor member. The proximal member may be a ring member.

In one embodiment the sleeve member is of a pliable material.

In one arrangement the sleeve extends from the proximal member, around the distal member and has a return section outside of the proximal member.

The return section may have a handle member such as a ring member.

In one embodiment the device comprises a guide member.

The retractor member may extend between the guide member and the proximal member.

The guide member may comprise a receiver for the proximal member.

The guide member may comprise a guide ring-receiving member.

The sleeve return section may be configured to provide an integral valve member. In this case the sleeve return section may be twisted to provide an iris valve.

In another embodiment the sleeve return section is mounted to the guide member.

The sleeve return section may be extended into the opening defined by the sleeve member.

The device may comprise a lock for locking the guide member to the proximal member. Typically the guide member is engagable with the proximal member to provide the lock.

The guide member may be an interference fit with the proximal member.

In one embodiment of the invention the device includes a valve, such as an iris-type valve.

In one embodiment the device comprises a biasing member for biasing the valve into a desired position such as the closed position.

In one arrangement the device comprises a guide member located proximally of the proximal member and a biasing means is provided between the proximal member and the guide member. The biasing means may comprise a spring such as a coil spring.

In one embodiment a sleeve member extends between the proximal member and the guide member and the biasing means is located around the sleeve. The sleeve member may be an extension of the retractor member.

In one embodiment the device comprises a release member for releasing the device from an incision. The release member may comprise an elongate member such as a pull ribbon or string extending from a distal end of the device.

The release member may extend from the distal member.

In one embodiment the valve is located or locatable proximal of the proximal member. A pliable material may be provided between the valve and the proximal member. The pliable material may comprise a proximal extension of the retractor member.

In one embodiment the pliable material comprises a sleeve section.

In another embodiment the valve is a lip seal.

The invention also provides a method for retracting an incision comprising the steps of:— providing a device comprising a retractor member having a distal portion and a proximal portion, a distal member associated with the distal portion and a proximal portion associated with the proximal portion;

inserting the distal member and the distal portion of the retractor member through an incision made in a patient; and pulling the retractor member axially relative to the distal member to draw the proximal and distal members towards one another thereby shortening the axial extent of the retractor member between the proximal and distal members and retracting the incision.

BRIEF DESCRIPTION OF THE DRAWINGS

The invention will be more clearly understood from the following description of some embodiments thereof, given by way of example only, with reference to the accompanying drawings, in which:

FIGS. 48 and 49 are cross sectional views of the device of FIG. 47 showing the formation of an iris valve;

FIGS. 52 to 55 are cross sectional views of another access port;

FIGS. 56 and 57 are cross sectional views of a further access port;

FIGS. 63 to 66 are cross sectional views of another access port;

FIGS. 60 to 72 are cross sectional views of another access port of the invention.

DETAILED DESCRIPTION

Figure 4:
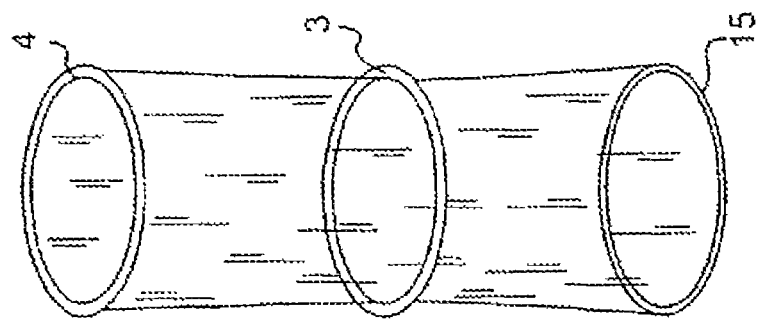
FIGS. 3 and 4 are perspective views illustrating the formation of the device of FIGS. 1 and 2.
Figure 3:
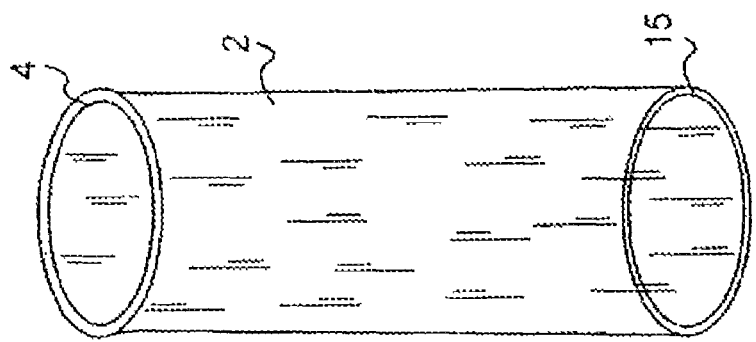
Figure 1:
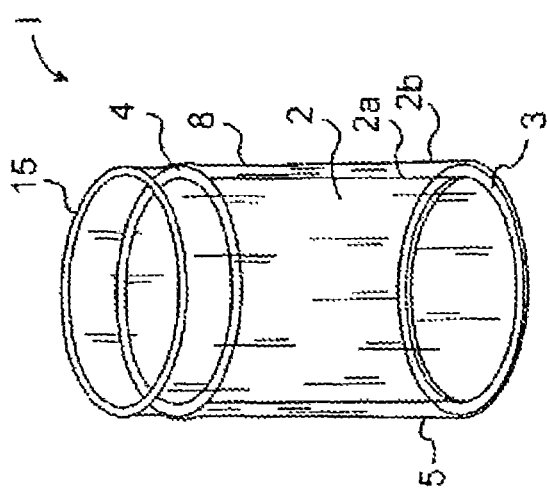
FIG. 1 is a perspective view of a retractor according to the invention.

Referring to the drawings, and initially to FIGS. 1 to 10 thereof there is illustrated a device 1 comprising a retractor member provided by a sleeve 2, a distal member provided by a distal ring 3 of resilient material such as an O-ring and a proximal member provided by a proximal ring 4 which may also be an O-ring.

The sleeve 2 is of any suitable material such as of pliable plastics film material and comprises a distal portion 5 for insertion through an incision 6, in this case made in a patient's abdomen 7, and a proximal portion 8 for extending from the incision 6 and outside of the patient.

In this case the distal ring 3 is not fixed to the sleeve 2 but rather the sleeve is led around the ring 3 and is free to move axially relative to the distal ring 3 somewhat in the manner of a pulley. The proximal ring 4 is fixed to the sleeve 2, in this case at the proximal inner end thereof. The sleeve 2 terminates in a handle or gripping portion which in this case is reinforced by a gripping ring 15.

Figure 6:
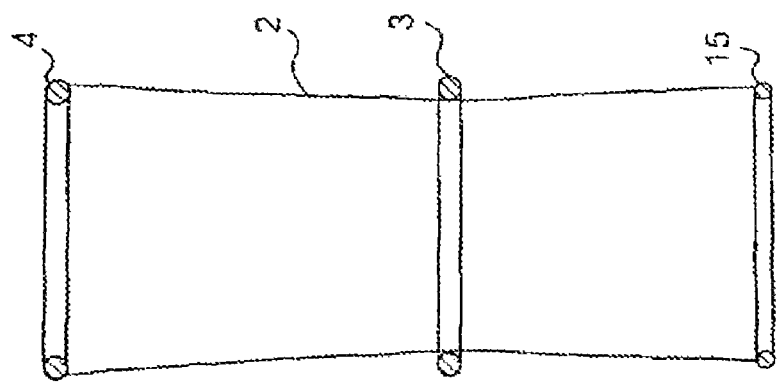
FIGS. 5 and 6 are cross sectional views of FIGS. 3 and 4 respectively.
Figure 5:
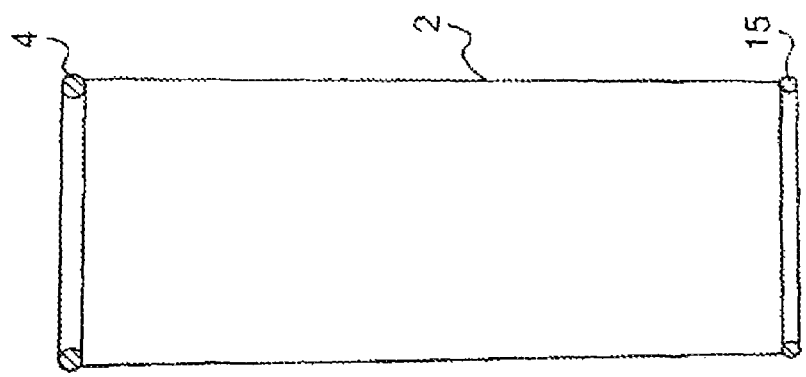
Figure 2:
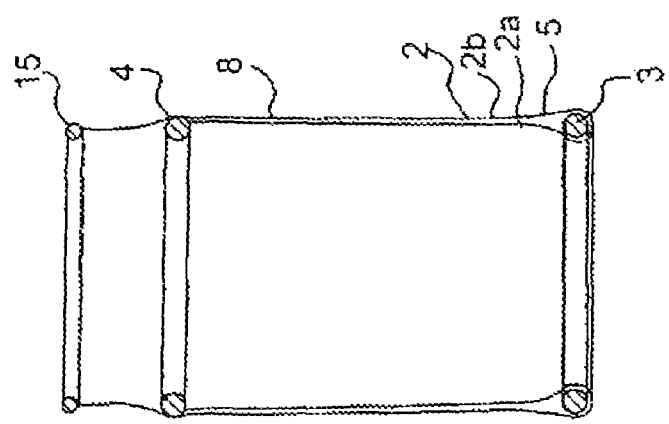
FIG. 2 is a cross sectional view of the device of FIG. 1.
Figure 7:
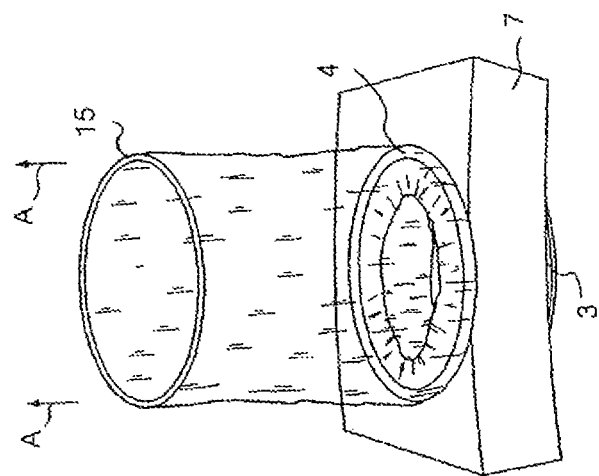
FIGS. 7 and 8 are perspective views illustrating the use of the device.
Figure 8:
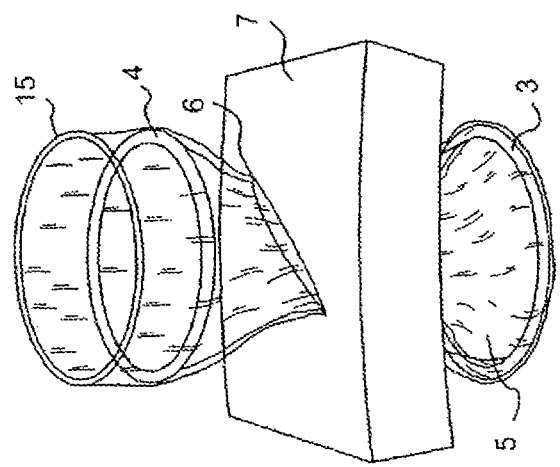
Figure 10:
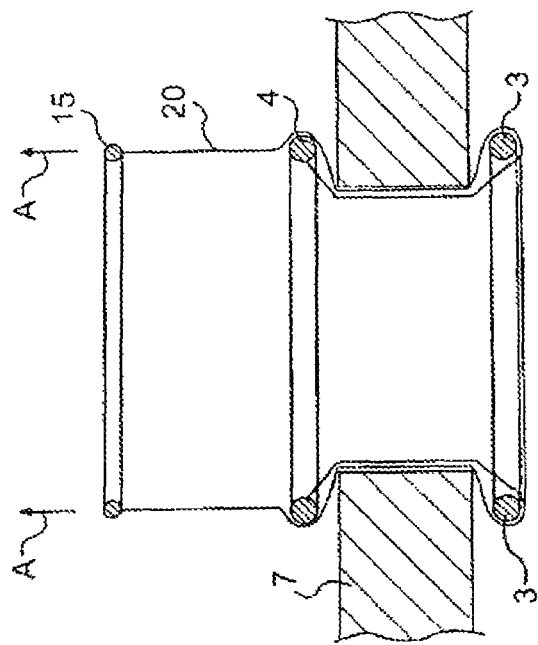
FIGS. 9 and 10 are cross sectional views illustrating the method of use of the device.
Figure 9:
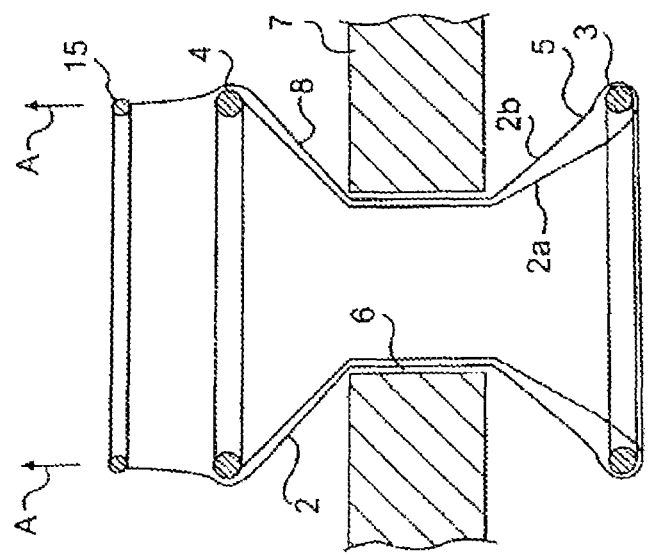
Figure 11:
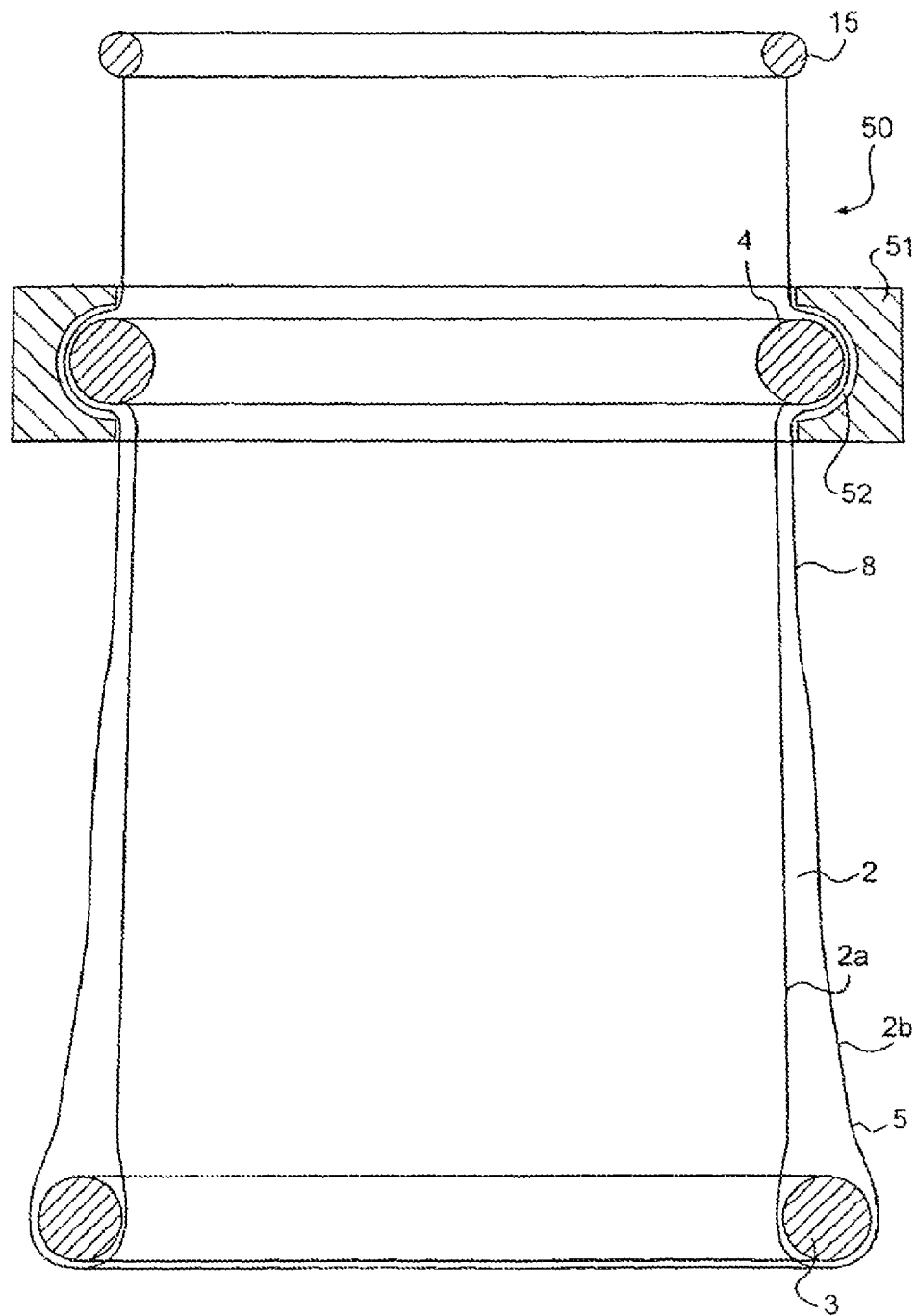
FIG. 11 is a cross sectional view of another device according to the invention in a configuration ready for use.
Figure 12:
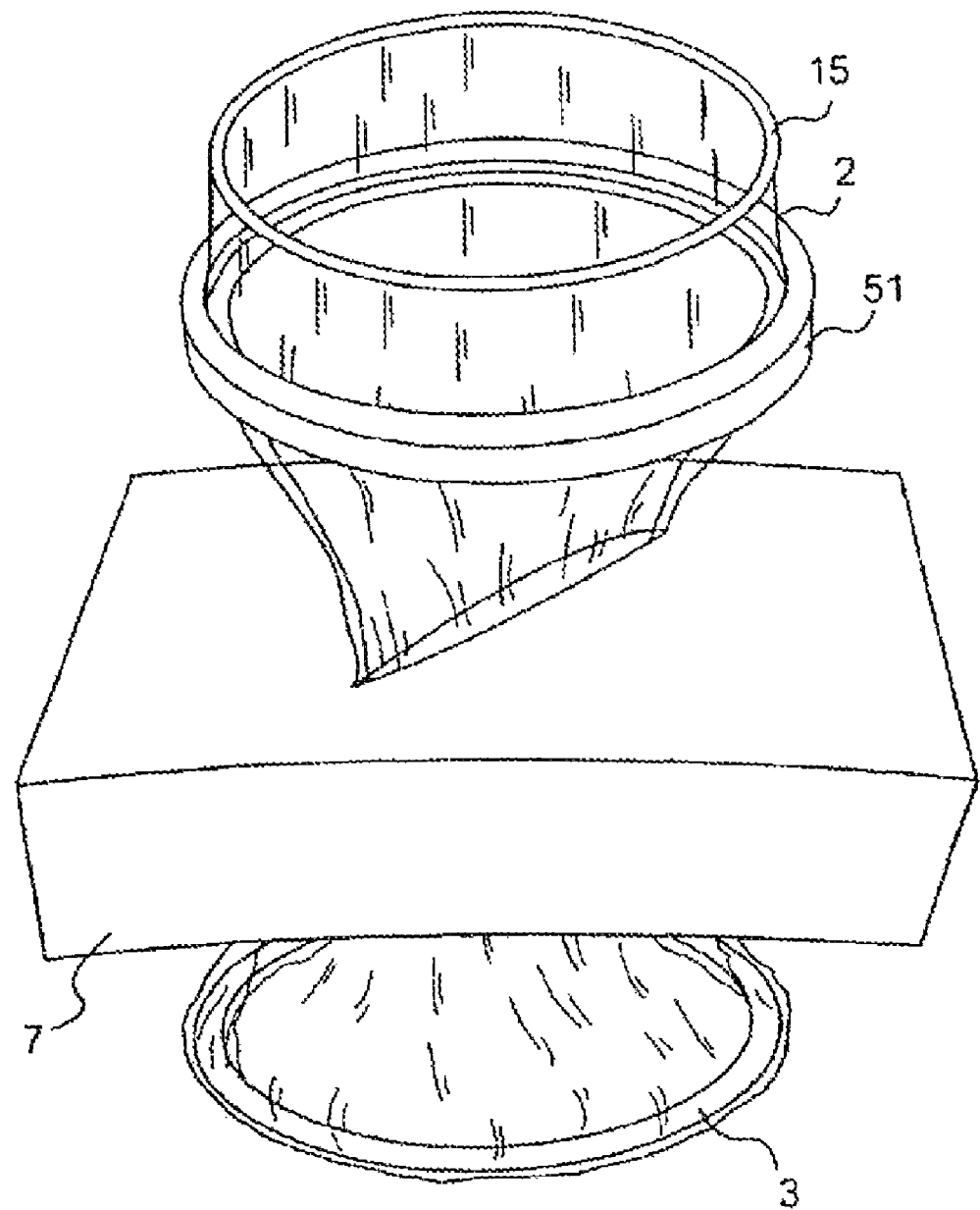
FIG. 12 is a perspective view of the device of FIG. 11 with a distal portion inserted through an incision.
Figure 13:
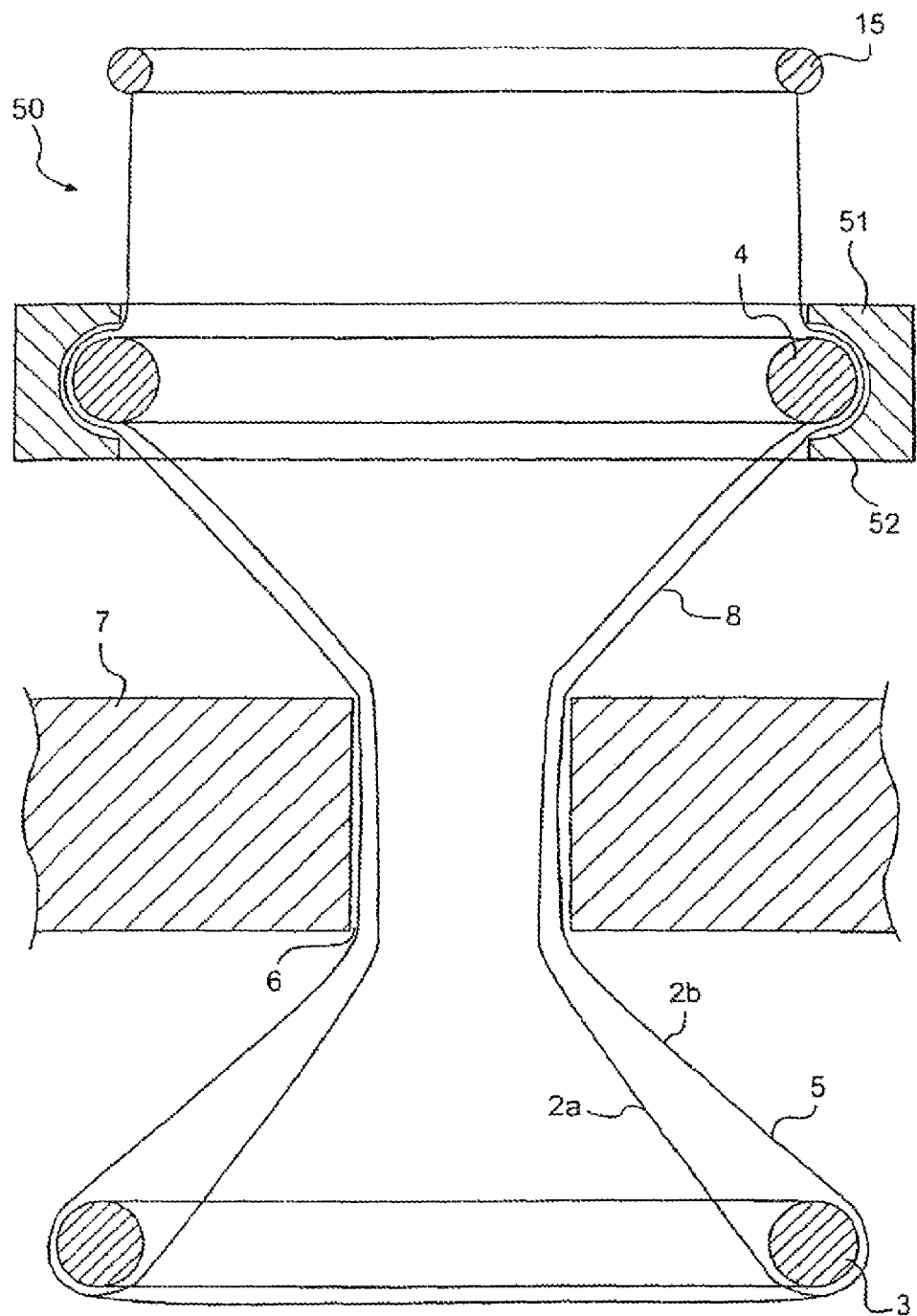
FIG. 13 is a cross sectional view of the device of FIG. 11 with a distal portion inserted through an incision.
Figure 14:
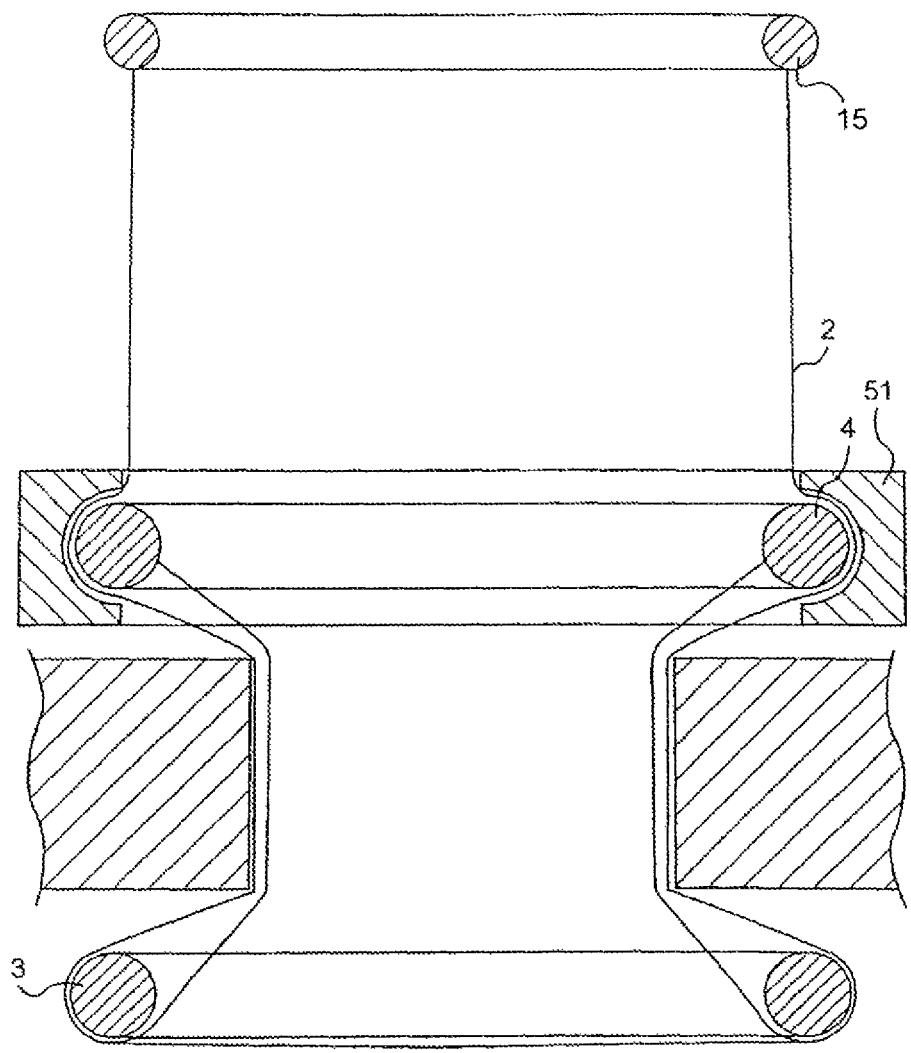
FIG. 14 is a cross sectional view of the device of FIG. 11 in use with an incision retracted.
Figure 15:
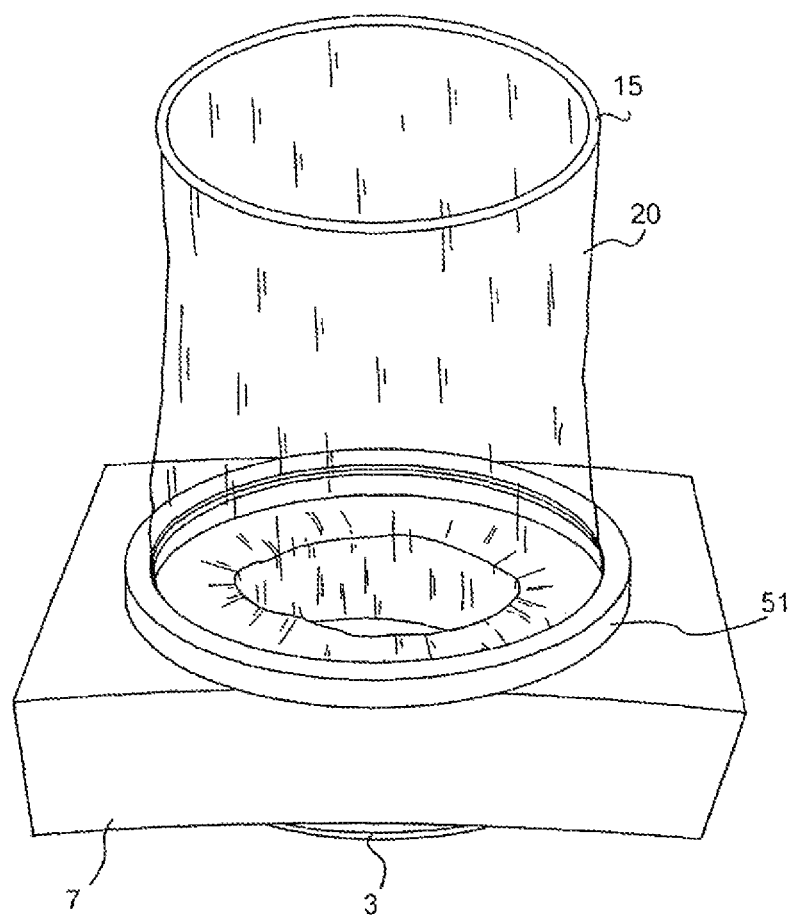
FIG. 15 is a perspective view of the device in the configuration of FIG. 14.

To configure the retractor device according to the invention a sleeve 2 is first provided with the gripping ring 15 fixed at one end and the proximal ring 4 fixed at the other end. The distal ring 3 is then placed over the sleeve 2 as illustrated in FIGS. 4 and 6. The gripping ring 15 is then used to manipulate the sleeve 2 so that the sleeve 2 is folded back on itself into the configuration of FIGS. 1 and 2 in which the gripping ring 15 is uppermost. The sleeve extends from the proximal ring 4 and the distal ring 3 is contained between inner and outer layers 2a, 2b of the sleeve 2. The device is now ready for use.

The resilient distal ring 3 is scrunched up and inserted through the incision 6 with the distal end 5 of the sleeve 2 as illustrated in FIG. 4. The sleeve 2 is then pulled upwardly in the direction of the arrows A in FIGS. 8 to 10. On pulling of the sleeve 2 upwardly the outer layer 2b is pulled up while the inner layer 2a is drawn around the proximal ring 3. This results in shortening the axial extent between the proximal ring 4 and the distal ring 3, tensioning the sleeve and applying a retraction force to the margins of the incision 6. The system appears to be self locking because when tension is applied to the sleeve 2 and the pulling force is released the rings 3, 4 remain in position with a retraction force applied. Frictional engagement between the layers of the sleeve in this configuration may contribute to this self locking.

As the incision is being retracted the margins are also protected by the sleeve. On retraction, an access port is provided, for example for a surgeon to insert his hand and/or an instrument to perform a procedure. The device may be used as a retractor in open surgery or as a base for a valve/seal to allow it to be used in hand assisted laparoscopic surgery or for instrument or hand access generally.

Excess sleeve portion 20 outside the incision may, for example, be cut-away.

The retractor is suitable for a range of incision sizes and is easily manufactured. It is also relatively easy to manipulate, in use. It not only retracts but also protects the incision.

Referring now to FIGS. 11 to 19 there is illustrated another device 50 according to the invention which is similar to the device described above with reference to FIGS. 1 to 10 and like parts are assigned the same reference numerals. In this case the device comprises a guide member 51 for the proximal ring 4. The guide member 51 is in the form of an annular ring member with an inwardly facing C-shaped groove 52 which is sized to accommodate the ring 4 as illustrated. The outer layer of the sleeve 2 is interposed between the ring 4 and the guide 51 to further control the pulling of the sleeve and thereby further controlling the application of the retraction force. The guide 51 also assists in stabilising the proximal ring 4. The use of the device 50 is illustrated in FIGS. 12 to 15 is similar to that described above.

Any suitable guide such as the ring 51 may be used to assist in retaining/stabilising the proximal ring 4 in a desired position during pulling up of the sleeve to retract the incision. The guide may be located proximal of the ring 4.

The guide member provides a monitoring member to which devices such as valves may be attached.

Figure 16:
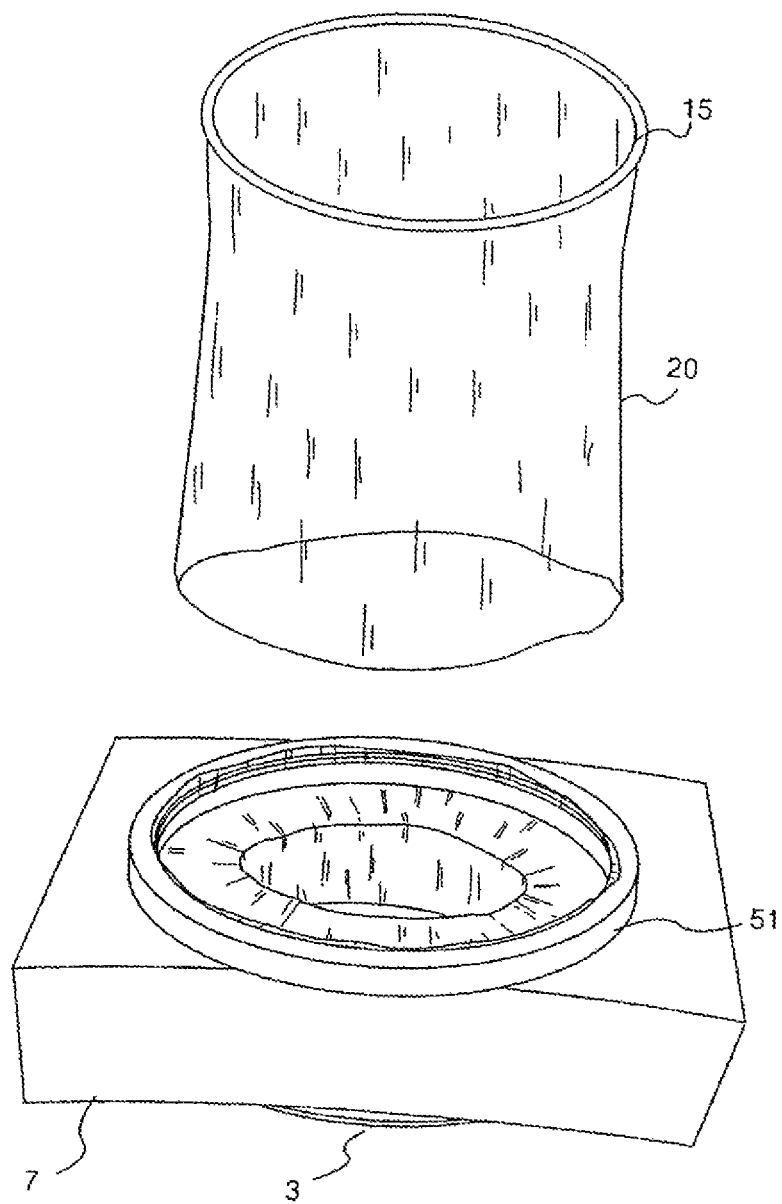
FIG. 16 is a perspective view of the device in situ with an excess sleeve portion being removed.

Referring to FIG. 16, it will be noted that in one case the excess sleeve portion 20 may be cut-away.

Figure 17:
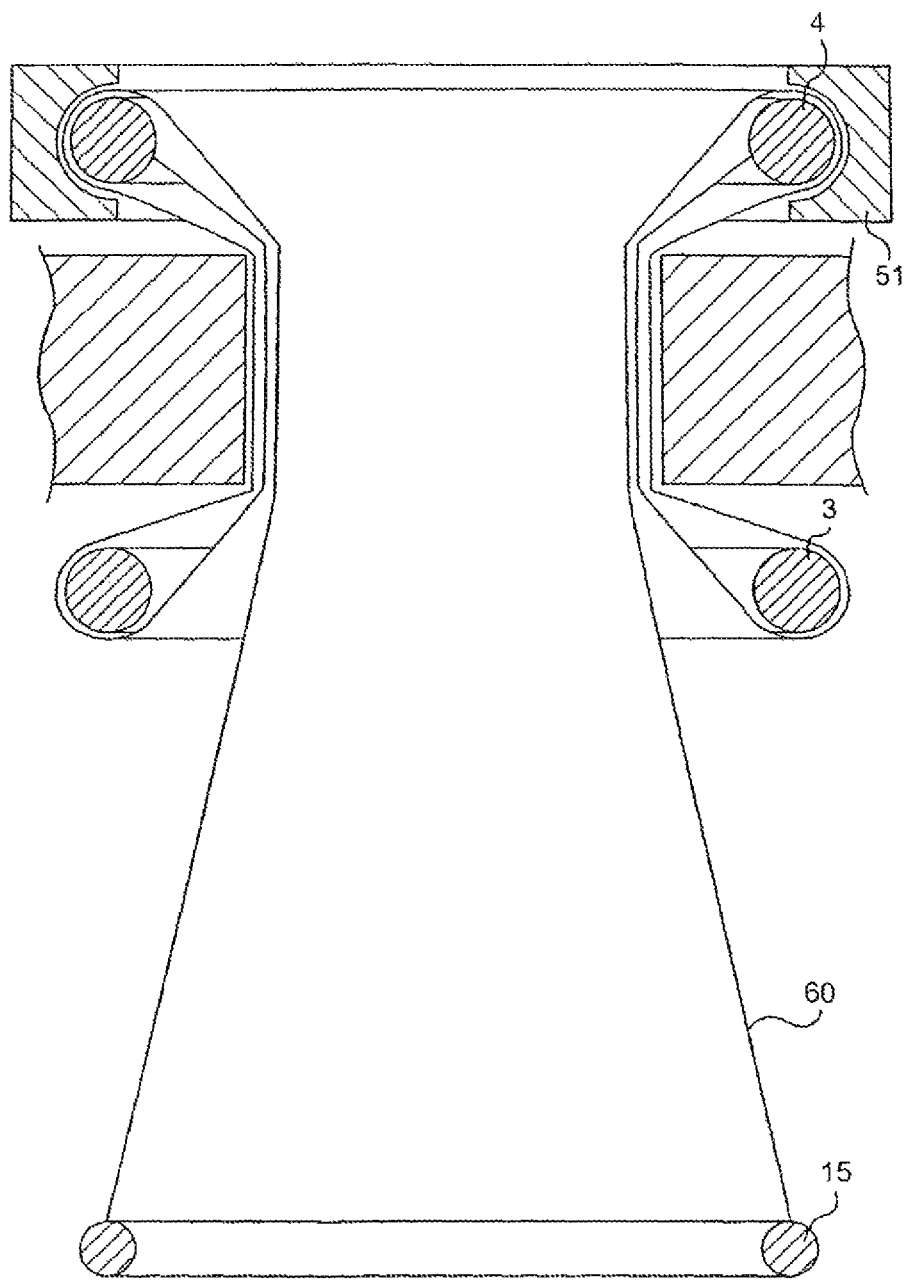
FIG. 17 is a cross sectional view of the device in situ with an excess sleeve portion extending back into the incision.

Referring to FIG. 17, in this case the excess sleeve portion is inverted 60 into the incision. In this configuration it may act as an organ retractor, or provide the surgeon with an open tunnel to work in.

Figure 18:
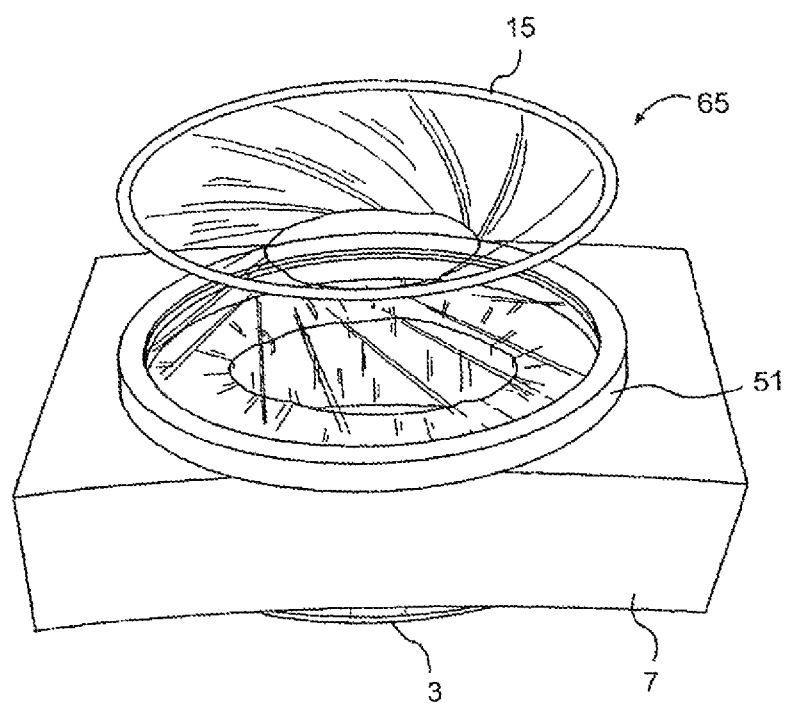
FIG. 18 is a perspective view of the device in situ with a excess sleeve portion being twisted.
Figure 19:
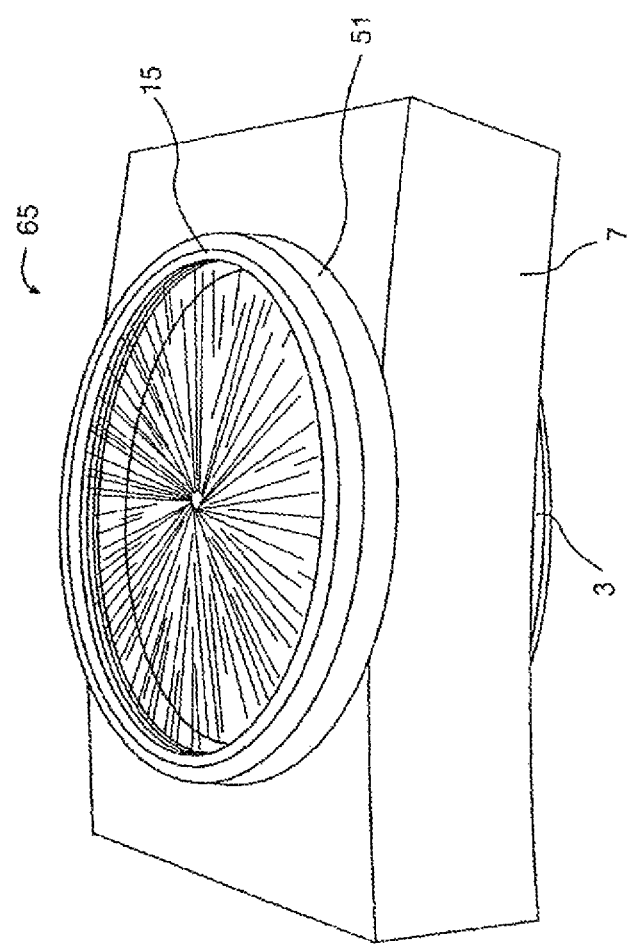
FIG. 19 is a perspective view similar to FIG. 18 with the excess sleeve portion further twisted to provide an iris valve.

Referring to FIGS. 18 and 19 in this case the excess sleeve portion is twisted to form an iris diaphragm valve 65.

Figure 20:
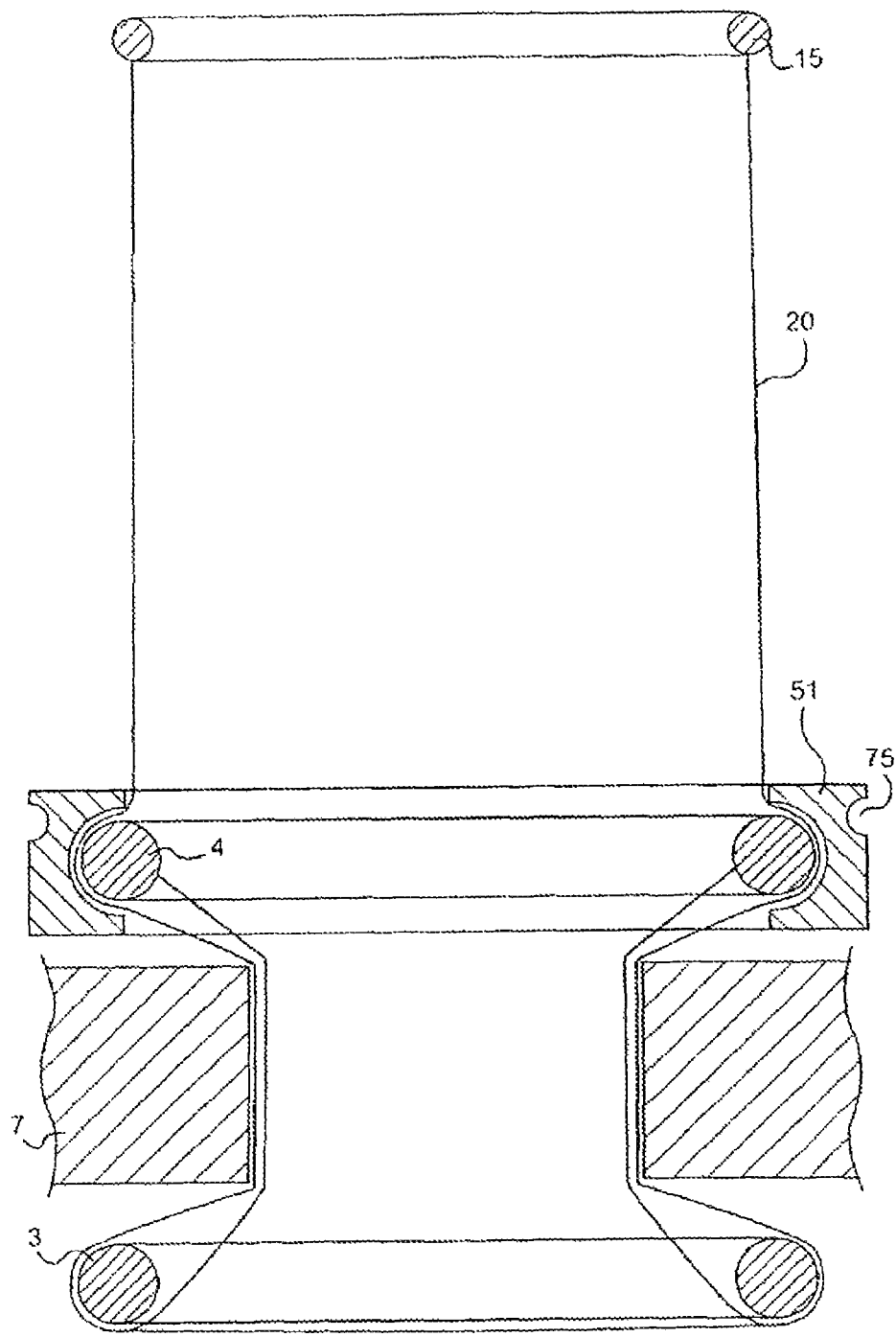
FIG. 20 is a cross sectional view of another device according to the invention in situ.
Figure 21:
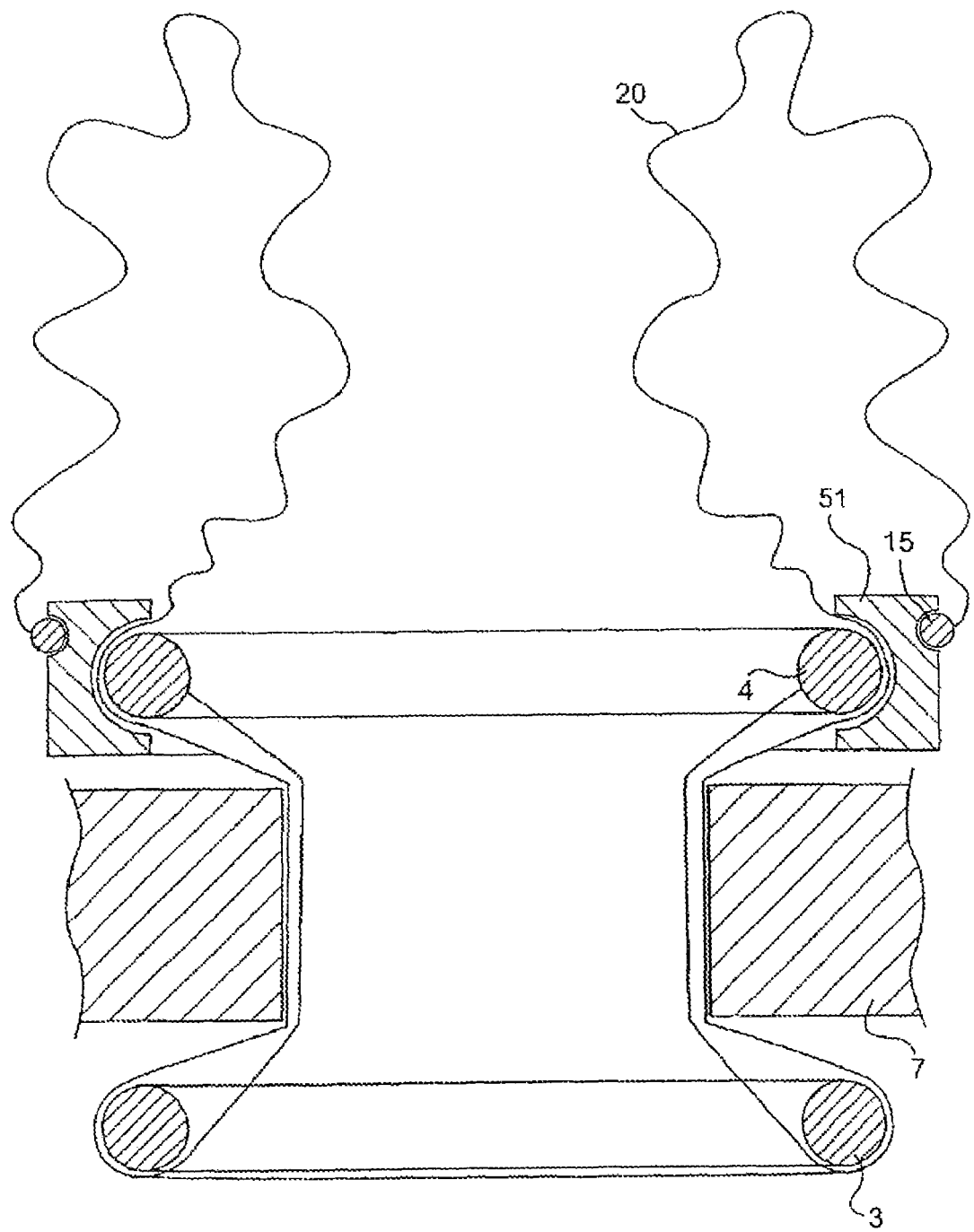
FIG. 21 is a cross sectional view of the device of FIG. 20 with an excess sleeve portion mounted to a guide member.
Figure 22:
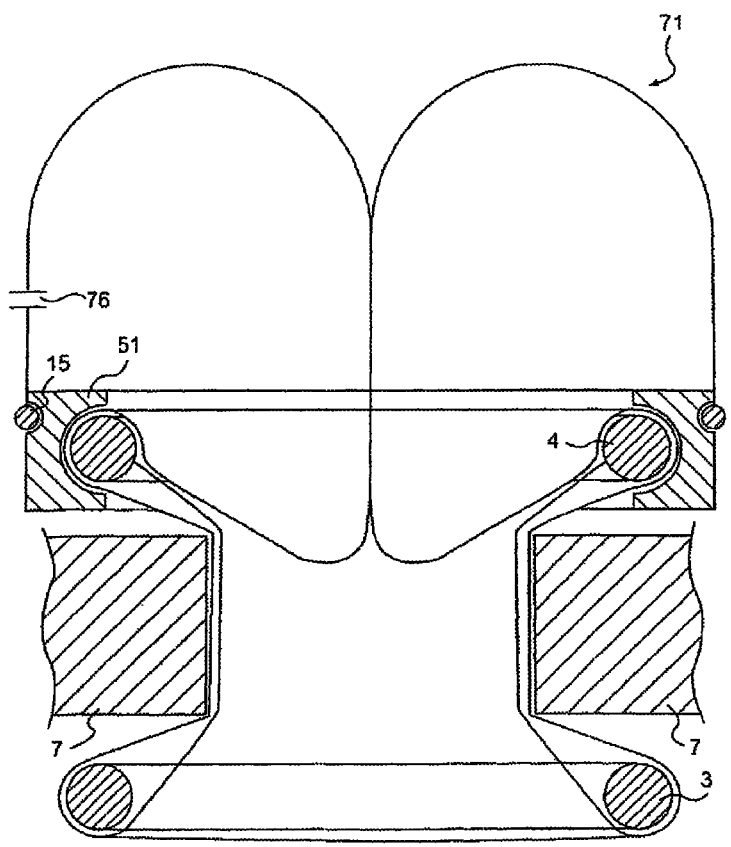
FIG. 22 is a cross sectional view of the device of FIG. 21 with the excess sleeve portion inflated to provide an integral everting access part.
Figure 25:
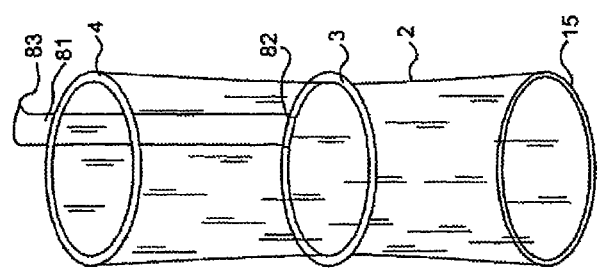
FIG. 25 is a perspective view illustrating the formation of the device of FIG. 23.
Figure 23:
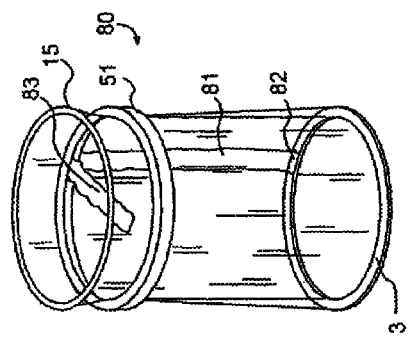
FIG. 23 is a perspective view of another retractor according to the invention incorporating a release device.
Figure 24:
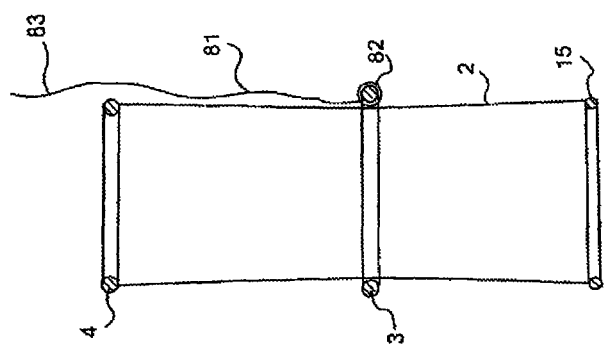
FIG. 24 is a cross sectional view of the retractor of FIG. 23.
Figure 26:
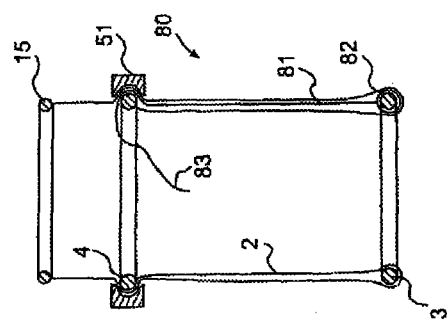
FIG. 26 is a cross sectional view of the device in the configuration of FIG. 25.
Figure 27:
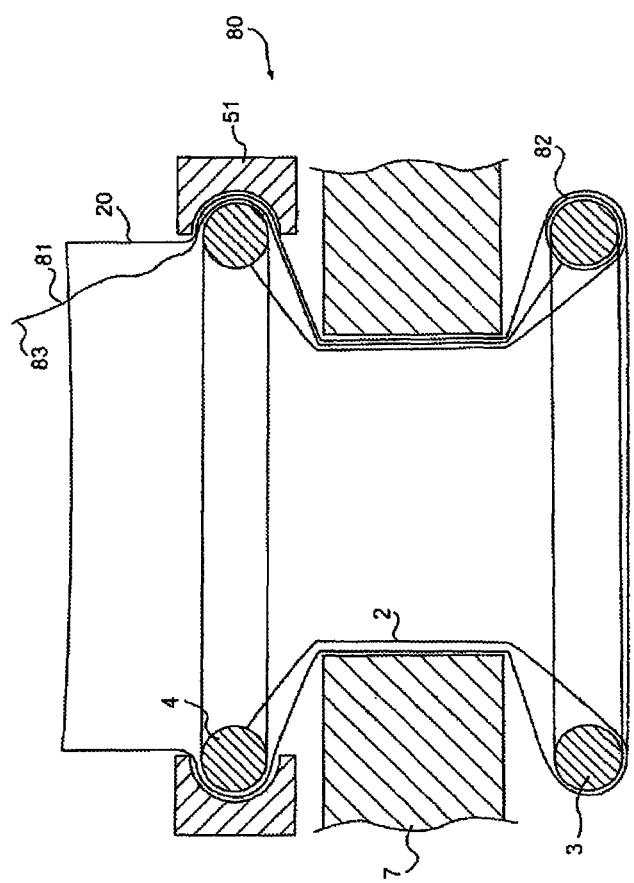
FIG. 27 is a cross sectional view of the retractor of FIGS. 23 to 26, in use.
Figure 28:
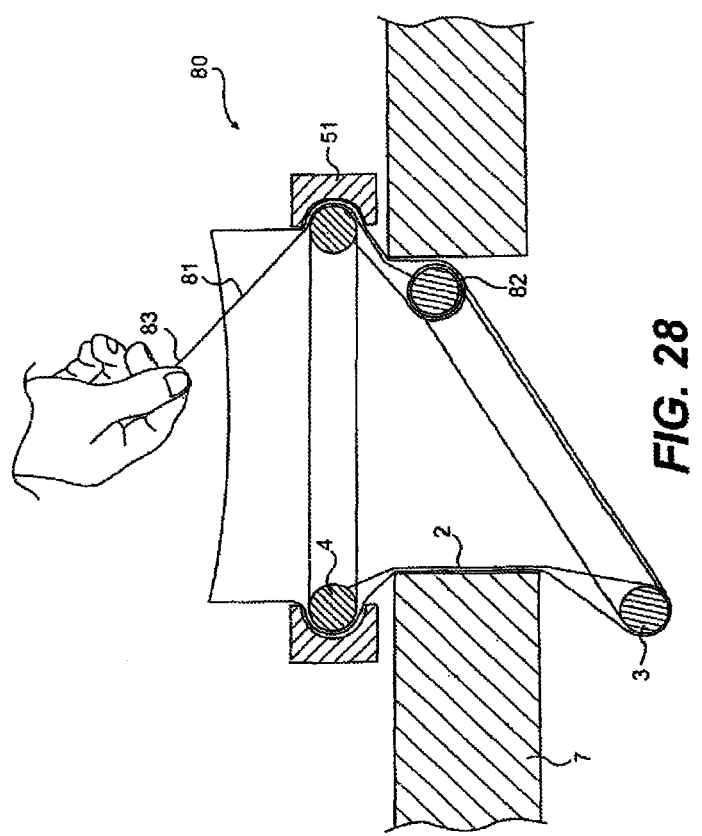
FIG. 28 is a cross sectional view of the retractor of FIGS. 23 to 27 illustrating the operation of a release device.
Figure 29:
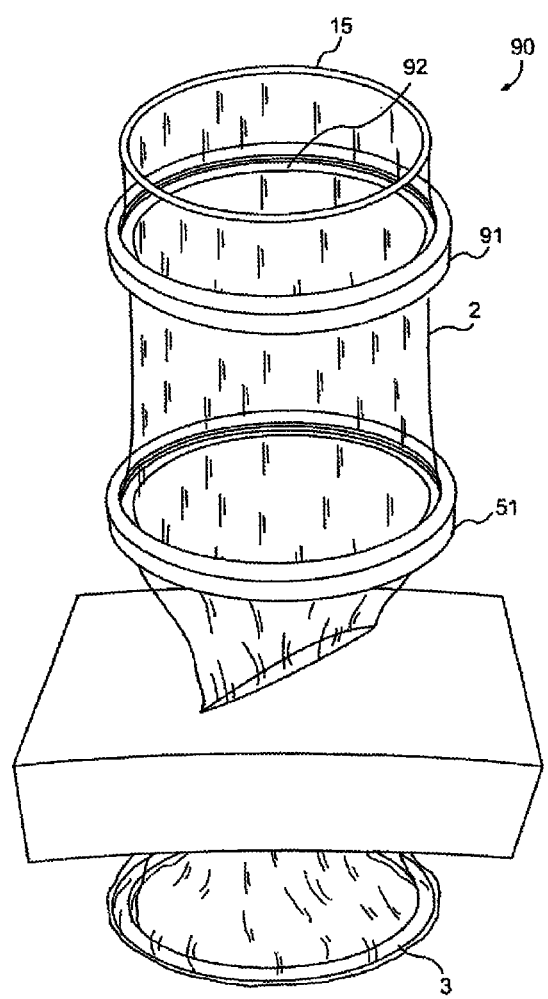
FIG. 29 is a perspective view of another device according to the invention in an insertion configuration.

In the embodiment illustrated in FIGS. 20 to 22 a device 70 according to the invention has an integral seal/valve 71. The device 70 is similar to that described above with reference to FIGS. 11 to 19 and like parts are assigned the same reference numerals. In this case the guide member 50 has an outer groove 75 to receive the gripping ring 15 as illustrated in FIG. 21. The excess sleeve portion 20 is folded out and down and the gripping ring 15 is engaged in the groove 75 to provide an air tight seal. In this configuration the excess sleeve may be inflated through an inflation port 76 to provide an integral access valve 71. The valve may be used to sealingly engage a hand, instrument or the like passing therethrough. The inflated sleeve portion defining the valve is evertable on passing an object therethrough.

Referring to FIGS. 23 to 28 there is illustrated another retractor 80 according to the invention which is similar to the retractors described above and like parts are assigned the same reference numerals. In this case the retractor 80 has a release mechanism which in this case is provided by a release cord or ribbon 81 which is coupled at one end 82 to the inner ring 3 and terminates in an outer free end 83 which may be grasped by a user. The ribbon 81, on assembly, is led through the gap between the proximal ring 4 and the outer guide member 51 so that it is positioned between the ring 4 and the guide member. The ribbon 81 facilitates release of the self locked sleeve in the in-use configuration sited in an incision. Pulling on the ribbon 81 pulls on the inner ring 3, allowing the ring 3 to be released from the inner wall of the incision to thereby release the device. The flexibility of the ring 3 facilitates this movement.

The advantage of this arrangement is that a user can readily release the device from its self locked retracting configuration.

Figure 30:
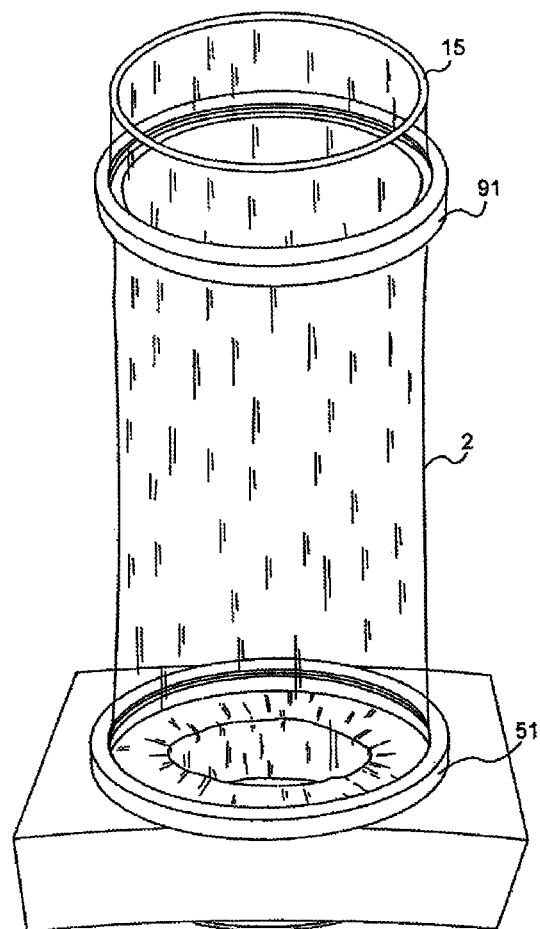
FIG. 30 is a perspective view of the device of FIG. 29 in position in an incision.
Figure 31:
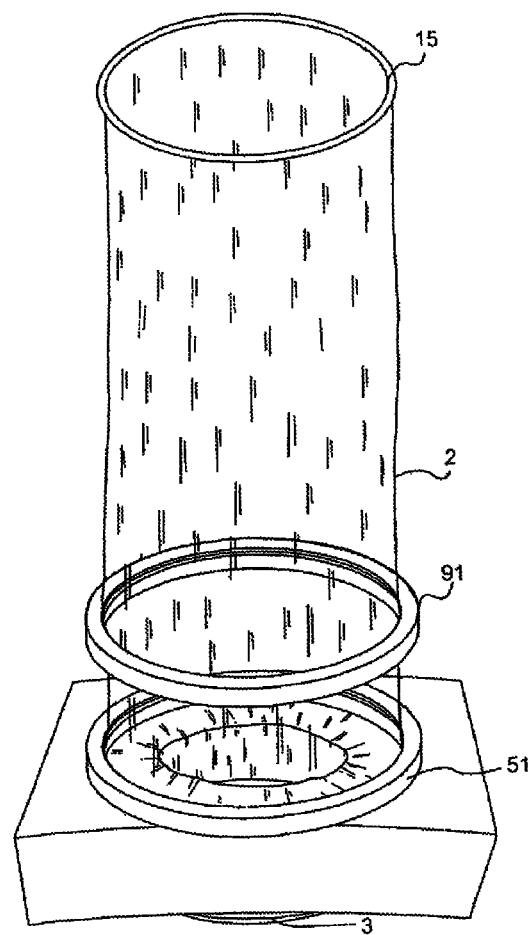
FIG. 31 is another perspective view of the device of FIG. 30 in another configuration.
Figure 32:
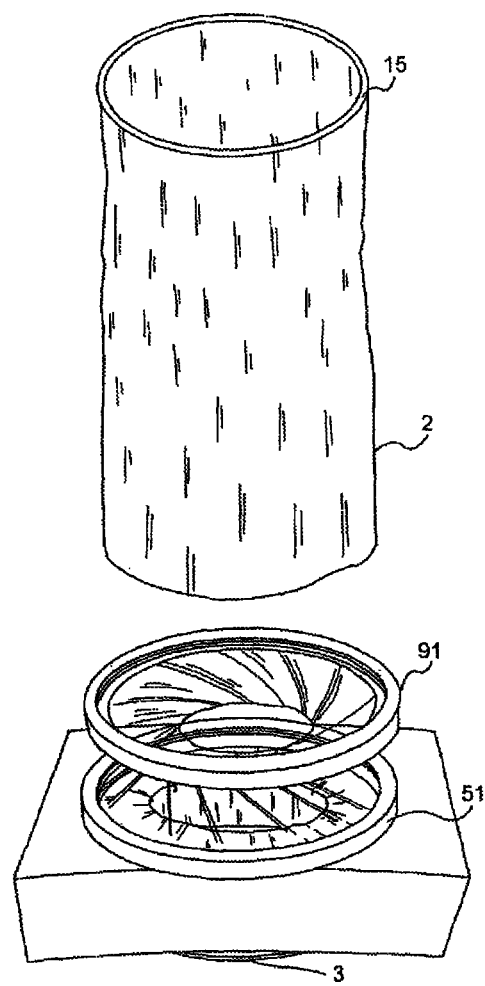
FIG. 32 is another view of the device of FIG. 31 with an outer portion severed and a valve being formed.
Figure 33:
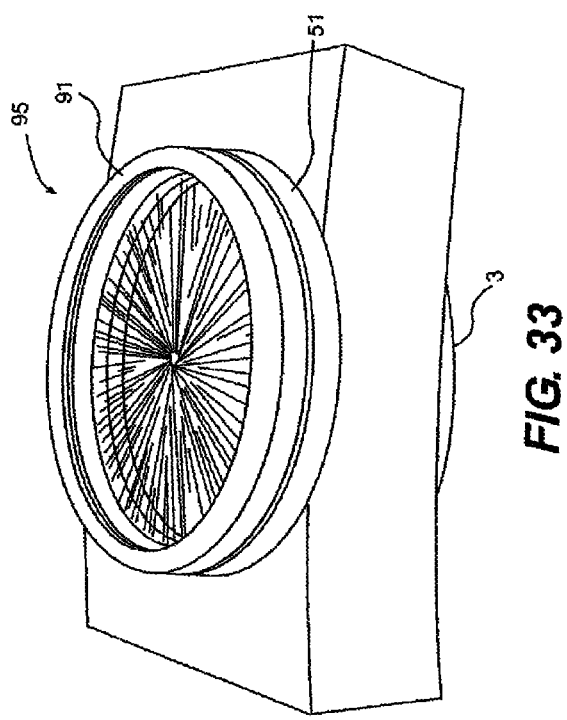
FIG. 33 is a view of the device of FIG. 32 with the valve closed.

Referring to FIGS. 29 to 33 there is illustrated another device 90 according to the invention in which parts similar to those of the devices described above are assigned the same reference numerals. In this case the device 90 has a lower guide ring 51 for the proximal ring 4 and an outer guide assembly provided by an upper guide ring 91 and a second proximal ring 92 between which the sleeve 2 is led. In all relevant embodiments the upper guide such as the ring 91 may provide a second mounting member located proximally of the first guide member such as the ring 51 which also provides a mounting member. The device is used to first retract an incision as described above. During this phase the outer guide assembly is conveniently external of the guide member 51 and proximal ring 4. Indeed, it may be completely detached from the sleeve 2 and subsequently coupled to the sleeve 2 at an appropriate stage such as when the incision is retracted as illustrated in FIG. 30. The outer guide assembly is then moved downwardly towards the incision as illustrated in FIG. 31. This may be achieved while pulling the sleeve 2 upwardly. When the guide assembly is adjacent to the guide member 51 excess sleeve length may be severed as illustrated in FIG. 32. By twisting the guide assembly relative to the guide member 51 the sleeve 2 is twisted, closing down the lumen of the sleeve 2 and forming an iris type access valve 95 as illustrated in FIG. 33. In this way a sealed access port is provided for hand and/or instrument access through the incision.

It will be appreciated that while reference has been made to an incision made by a surgeon the devices of the invention may be applied for retraction of any opening such as a body opening.

Figure 34:
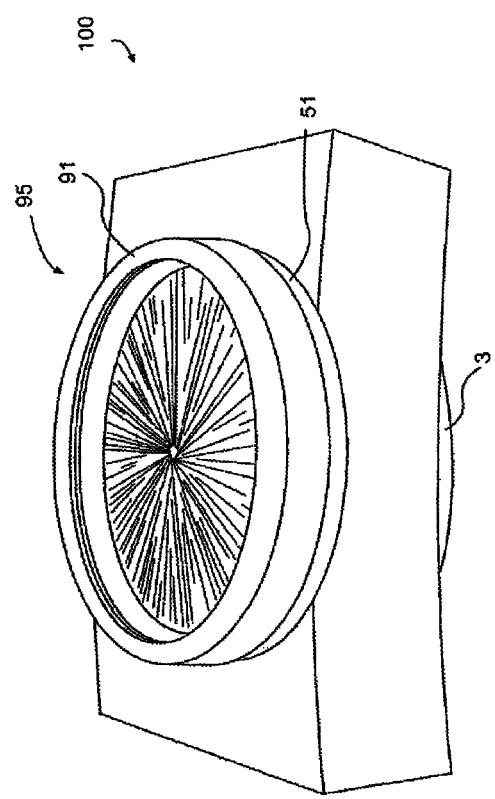
FIG. 34 is a perspective view of another device similar to the device of FIGS. 29 to 33 with a valve closed.
Figure 35:
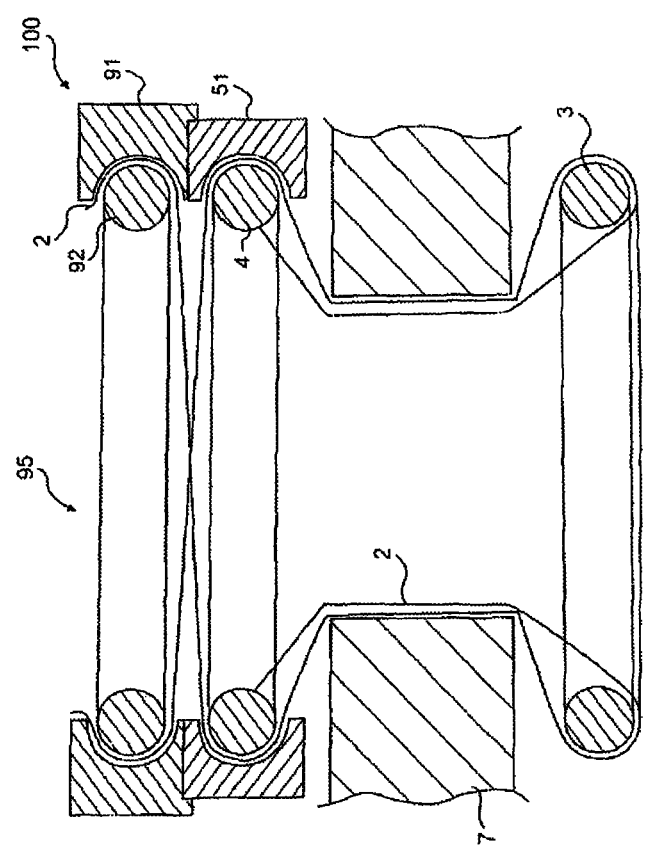
FIG. 35 is a cross sectional view of the device of FIG. 34.
Figure 36:
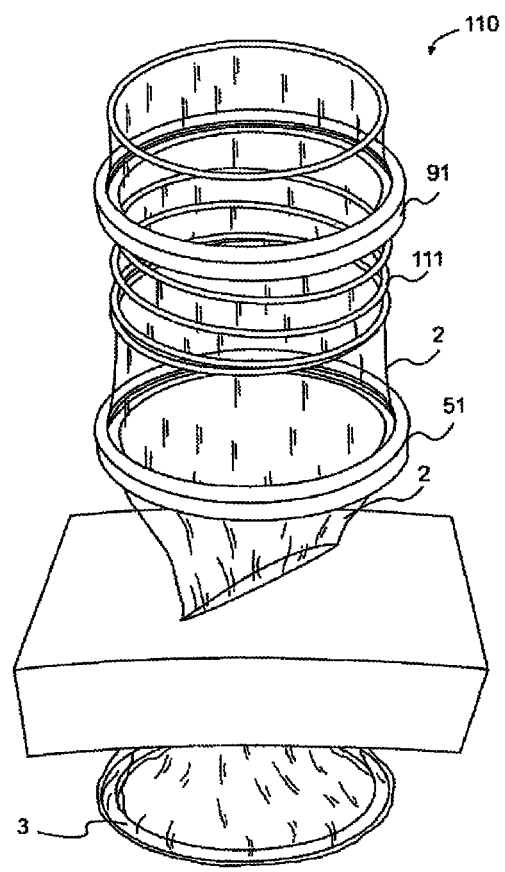
FIG. 36 is a perspective view of another device similar to the device of FIGS. 29 to 33 incorporating a biassing means in an inserted configuration.
Figure 37:
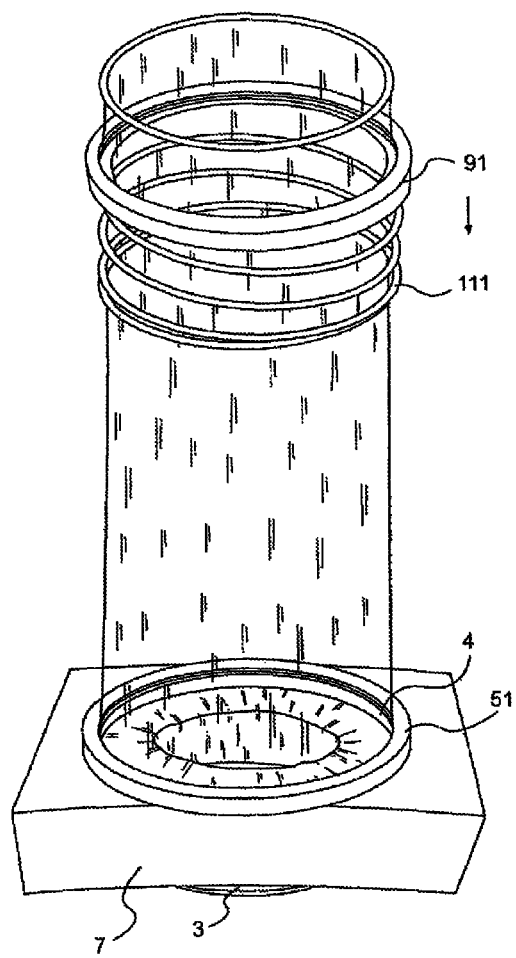
FIG. 37 is another perspective view of the device of FIG. 36 in a retracting configuration.
Figure 38:
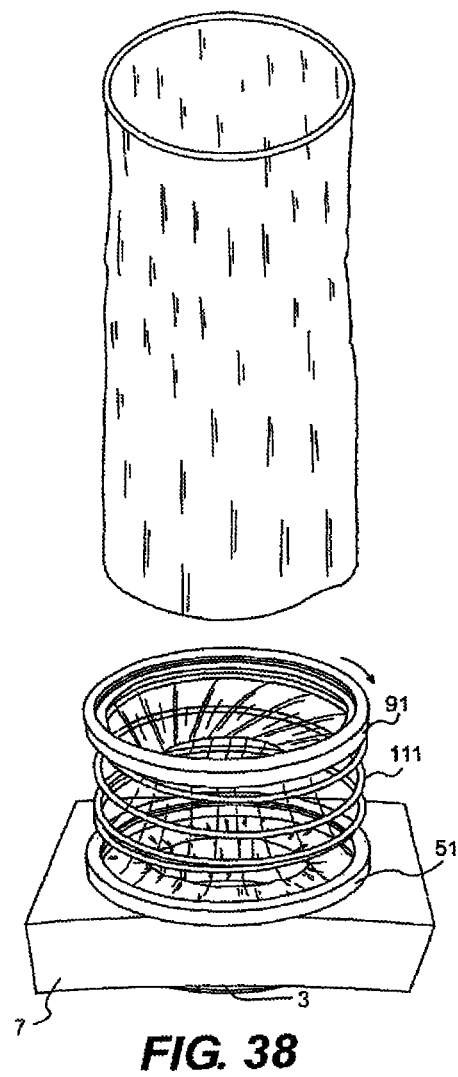
FIG. 38 is a perspective view of the device of FIG. 37 in another configuration and excess sleeve being removed.

Referring to FIGS. 34 and 35 there is illustrated another retractor device 100 according to the invention which is similar to the device of FIGS. 29 to 33 and like parts are assigned the same reference numerals. In this case a releasable lock is provided to maintain the access valve 95 closed. For interlocking, in this instance the upper guide ring 91 is an interference fit with the lower guide ring 51. Various other locking arrangements may be used such as a screw threaded or bayonet type engagement, magnets, clips and the like.

Figure 39:
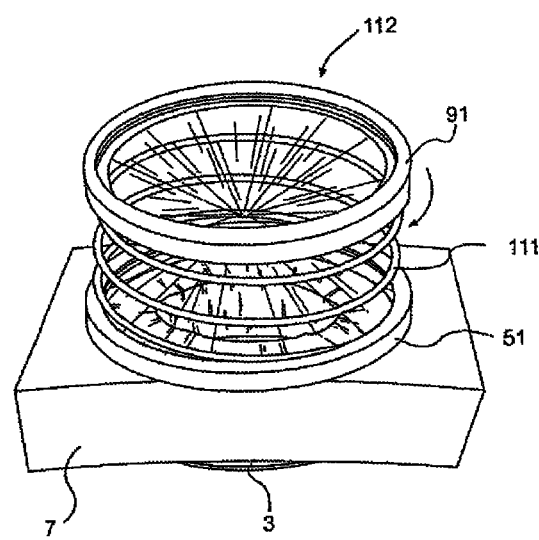
FIG. 39 is a perspective view of the device of FIG. 38 with a valve closed.
Figure 40:
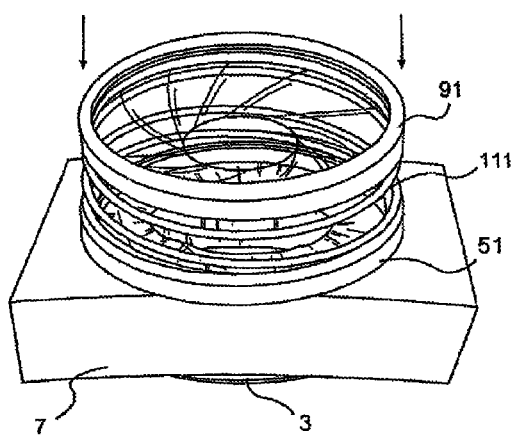
FIG. 40 is a perspective view of the device of FIG. 39 with a valve partially open.
Figure 41A:
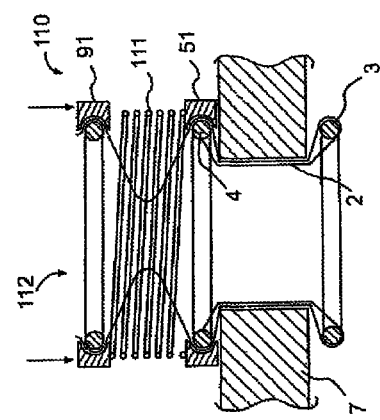
FIGS. 41A and 41B are perspective views of the device of FIG. 39.
Figure 41B:
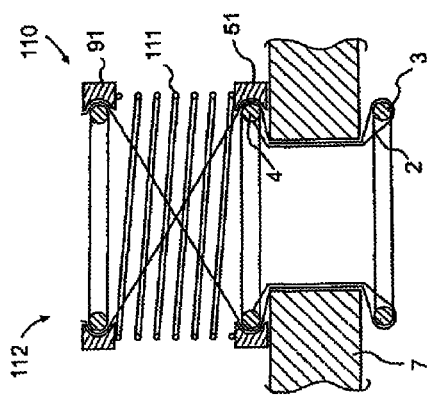
Figure 41C:
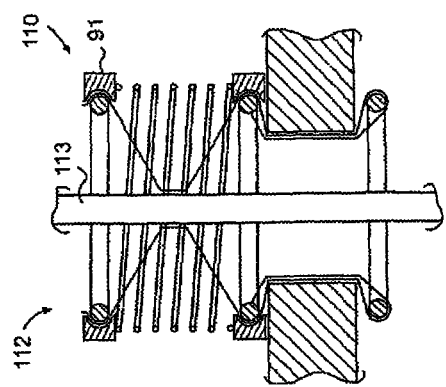
FIGS. 41C and 41D are perspective views of the device of FIG. 39 with an object inserted through the valve.
Figure 41D:
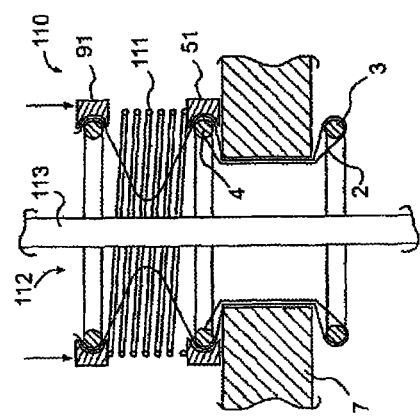
Figure 43:
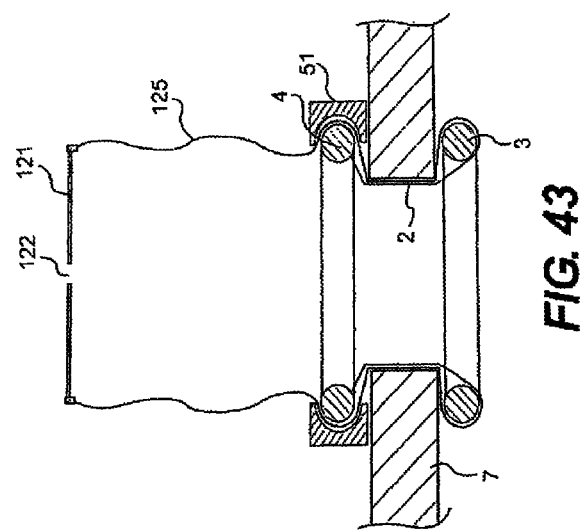
FIG. 43 is a cross sectional view of the device of FIG. 42 in position in an incision.
Figure 42:
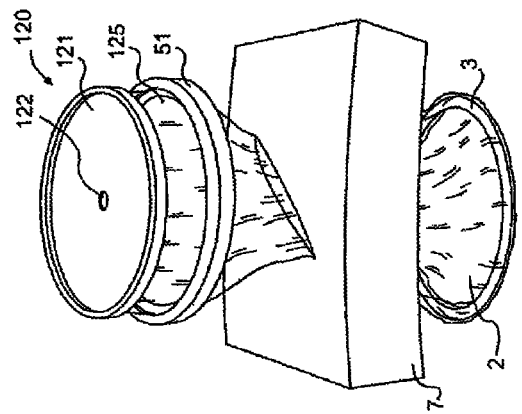
FIG. 42 is a perspective view of another device according to the invention.
Figure 44:
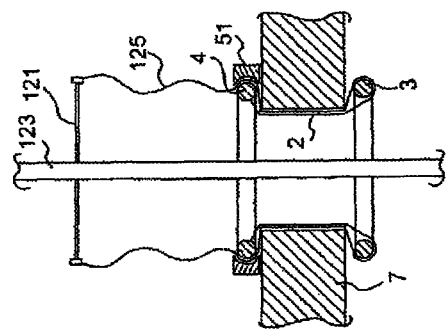
FIG. 44 is a cross sectional view of the device of FIG. 43 with an object extending therethrough.

Referring to FIGS. 36 to 41D there is illustrated another retractor device 110 according to the invention which is similar to the device of FIGS. 29 to 33 and like parts are assigned the same reference numerals. In this case the device incorporates a biassing means to bias an integral valve into a closed position. The biassing means is in this case provided by a coil spring 111 which is located around the sleeve between the guide rings 51, 91. In use, the device is used in a similar manner to the device of FIGS. 29 to 33 except that on movement of the upper guide ring 91 downwardly the spring 111 also moves downwardly towards the lower guide ring 51, initially into the position illustrated in FIG. 38. Excess sleeve material may be removed at this stage. The spring 111 is tensioned as the upper ring 91 is rotated while pushing the upper ring 91 downwardly. The sleeve material between the two rings 51, 91 is twisted, forming an iris type valve 112 as illustrated in FIG. 39. To open the valve 112 to pass an object such as an instrument, hand, arm or the like therethrough a downward force may be applied to push the upper ring 91 towards the lower ring 51 against the biassing of the spring. This configuration is illustrated in FIG. 40. When the object is inserted the upper ring member 91 is released, allowing the valve to close around the object. The operation of the device 110 will be readily apparent from FIGS. 41A to 41D. In FIG. 41A the valve 112 is illustrated in a closed resting configuration. FIG. 41B shows the application of a downward force to open the valve 112. An object such as an instrument 113 is shown inserted through the open valve 112 in FIG. 41C. In FIG. 41D the downward pressure on the upper ring 91 is released allowing the valve 112 to close around the object 113.

Figure 45:
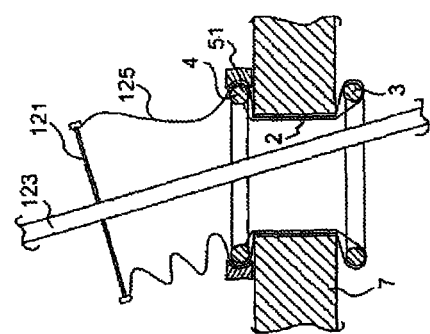
FIG. 45 is a cross sectional view similar to FIG. 44 with an object offset from a longitudinal axis of the device.

Referring now to FIGS. 42 to 45 there is illustrated another device 120 according to the invention which has some aspects similar to the device of FIGS. 11 to 18 and like parts are assigned the same reference numerals. In this case the device has a lip seal 121. The lip seal 121 is provided by a membrane with a central aperture 122 through which an object 123 such as an instrument is passed. The lip seal 121 is located on the sleeve 2 proximally of the guide ring 51 such that a proximal flexible sleeve section 125 is provided. This sleeve section 125 is very useful in facilitating offset movements of the object 123 as illustrated in FIG. 45. The sleeve section 125 accommodates movement of the object 123 whilst maintaining sealing engagement between the lip seal 121 and the object 123. It will be appreciated that this feature, as with several other features described above may be utilised in association with other constructions of wound protector/retractors and access parts generally other than those illustrated in the drawings.

Figure 47:
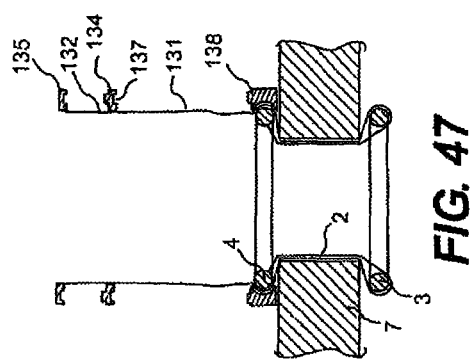
FIG. 47 is a cross sectional view of the device of FIG. 46 with an incision retracted.
Figure 46:
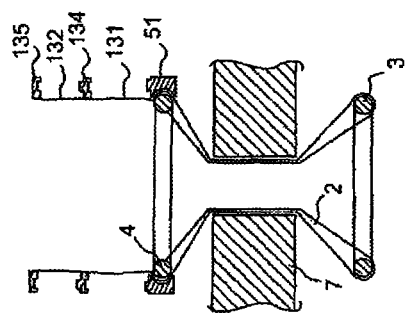
FIG. 46 is a cross sectional view of another device according to the invention on insertion into an incision.
Figure 50:
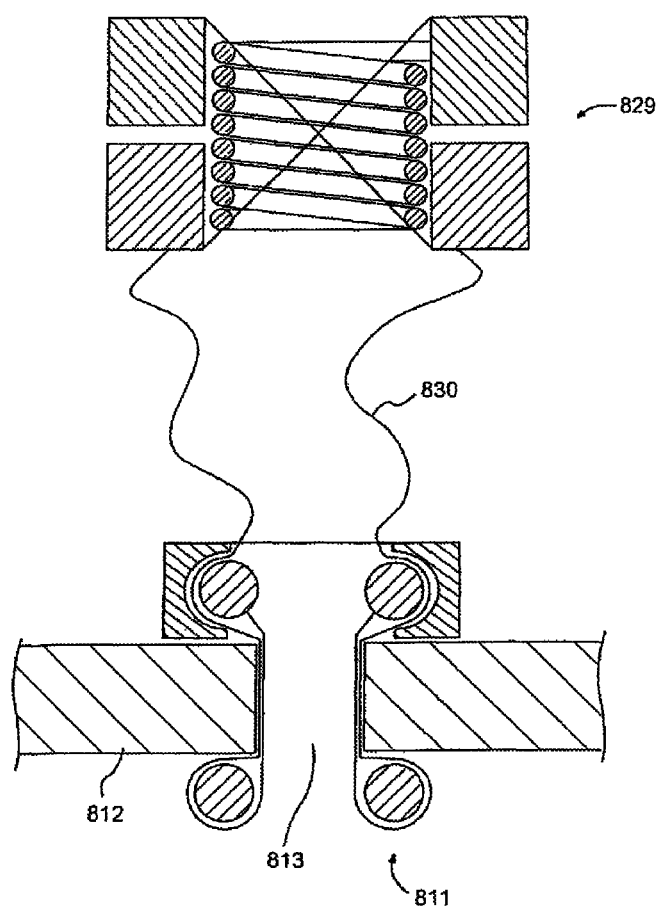
FIG. 50 is a cross sectional view of another access port.
Figure 51:
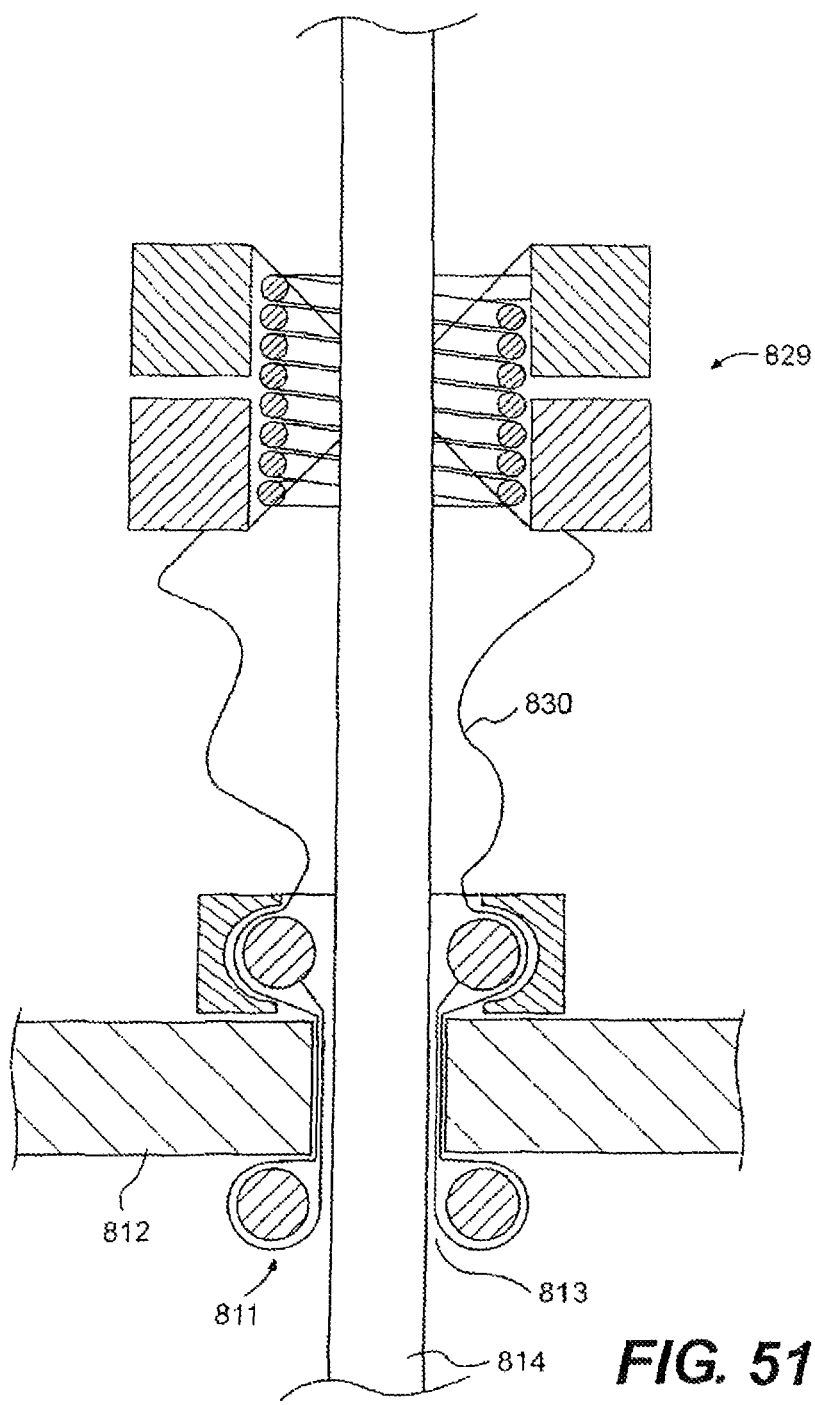
FIG. 51 is a cross sectional view of the port of FIG. 50 with an instrument in position.
Figure 53:
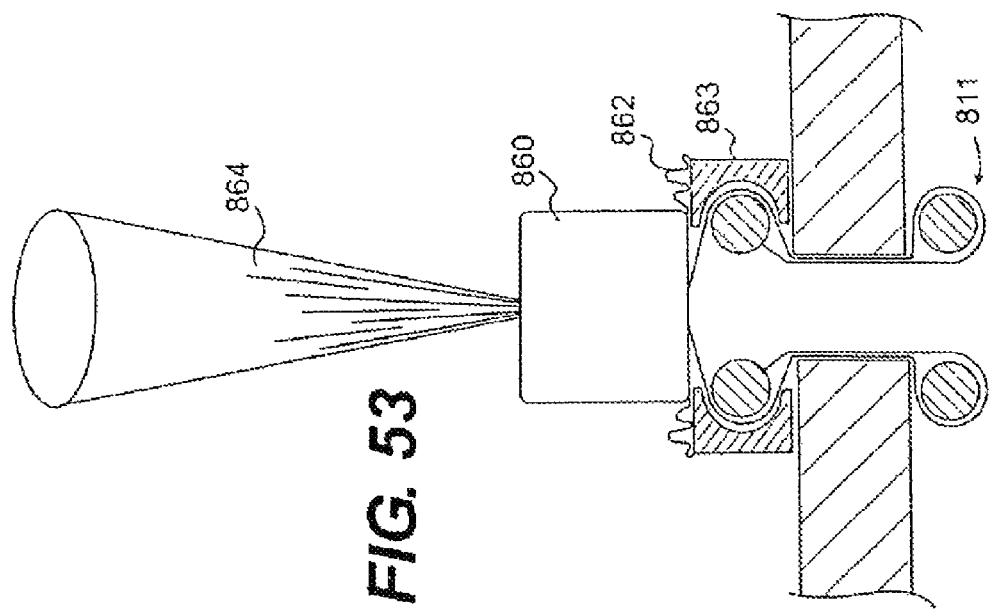
Figure 52:
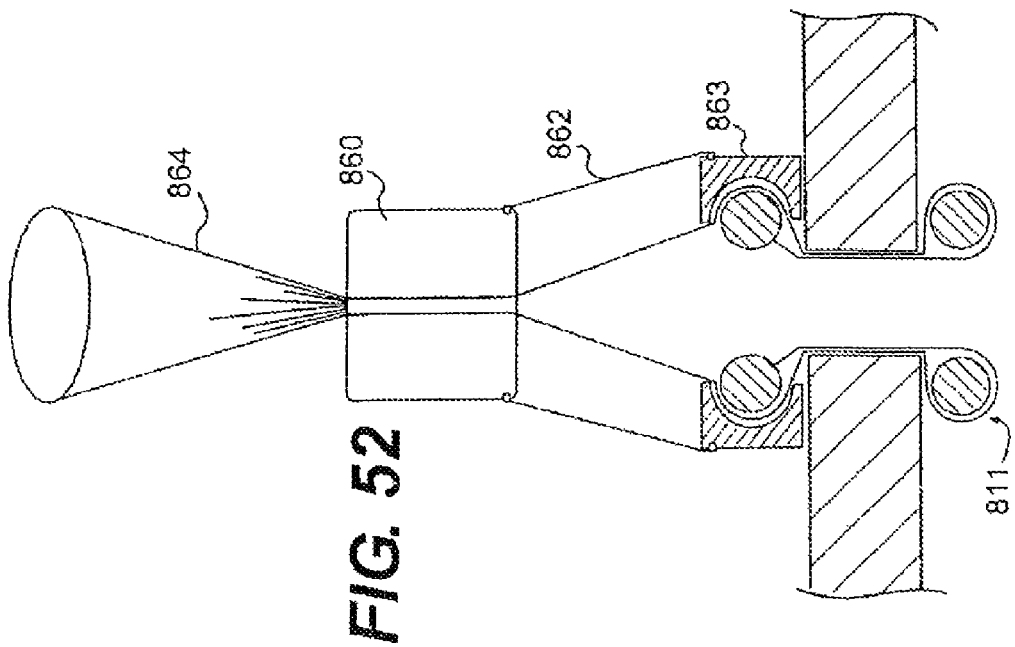

Referring to FIGS. 46 to 48 there is illustrated another device 130 according to the invention which has some features similar to those of FIGS. 11 to 15, like parts being assigned the same reference numerals. In this case the sleeve has a proximal section external of the wound when the device is in the retracting configuration. This proximal sleeve section comprises a first portion 131 extending from the guide ring 51 and a second portion 132 extending from the first portion 131. The second portion 132 is defined between two spaced-apart iris rings 134, 135. It will be noted that the iris rings 134, 135 have engagement features such as projections and grooves for interengagement on assembly. The iris ring 134 also has an engagement element, in this case provided by a groove 137 for engagement on assembly with a corresponding engagement element of the guide ring 51 which in this case is provided by a projection 138.

The device is fitted as described above to retract an incision, leaving the first and second sleeve portions 131, 132 extending proximally. The first sleeve portion 131 is redundant and can be removed or scrunched up on assembly of the first iris ring 134 to the guide ring 138 as illustrated in FIG. 48. The second or upper iris ring 135 is then rotated to twist the sleeve section 132 to form an iris-type seal as illustrated in FIG. 49. The iris ring 135 is engaged with the iris ring 134 as illustrated to maintain the valve closed.

In some of the embodiments described above a valve 829 is mounted directly to a retractor base 811. It is possible to provide a flexible coupling between the retractor 811 and the valve 829. For example, as illustrated in FIGS. 93 and 94 such a flexible coupling is provided by a length of flexible sleeve 830 extending between the retractor 811 and the valve 829. The flexible sleeve 830 may be formed by excess retractor sleeve material attached to the valve 829.

In a further embodiment of the invention as illustrated in FIGS. 52 to 57 a valve 860 may be coupled to the retractor 811 in such a way as to facilitate a flexible joint therebetween. For example, a fixed length sleeve 862 may extend between an outer proximal ring 863 of the retractor 811 and the valve 860. Excess sleeve material 864 from the retractor 811 may pass up through the valve 860. The valve 860 may be pushed down and the excess sleeve pulled up to firmly lock the base retractor 811 in the incision. Excess sleeve material 864 may be cut-away and removed, if desired. The flexible sleeve 864 allows the instrument to tilt as illustrated in FIG. 57 without compromising the valve seal to the shaft of the instrument/object 814.

Figure 59:
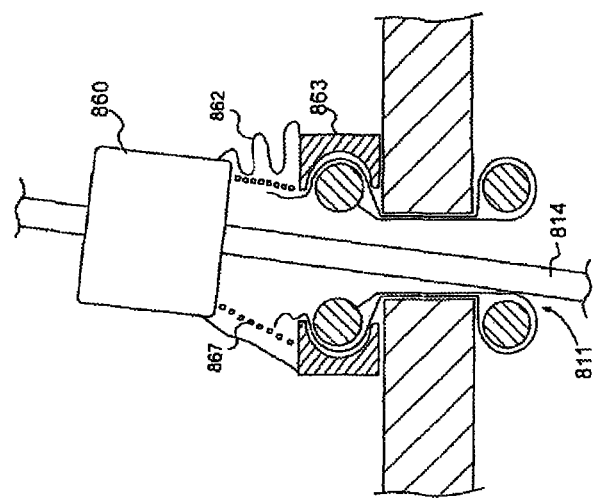
FIGS. 58 and 59 are cross sectional views of another access port.
Figure 58:
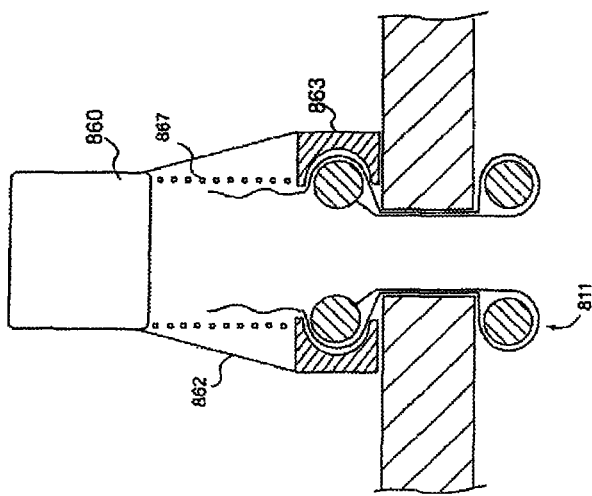

As illustrated in FIGS. 58 and 59 a spring 867 may be provided between the valve 860 and the retractor proximal ring 863 for more controlled flexibility.

Figure 61:
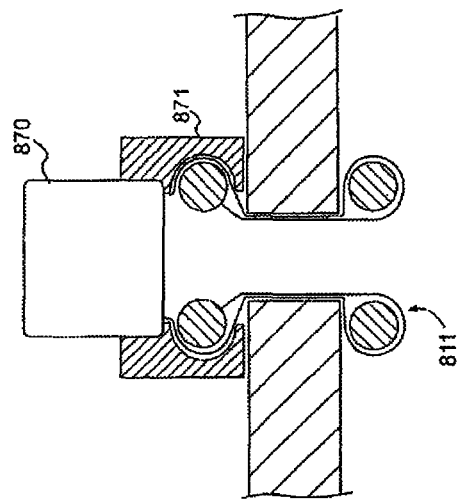
FIGS. 60 to 62 are cross sectional views of a further access port.
Figure 60:
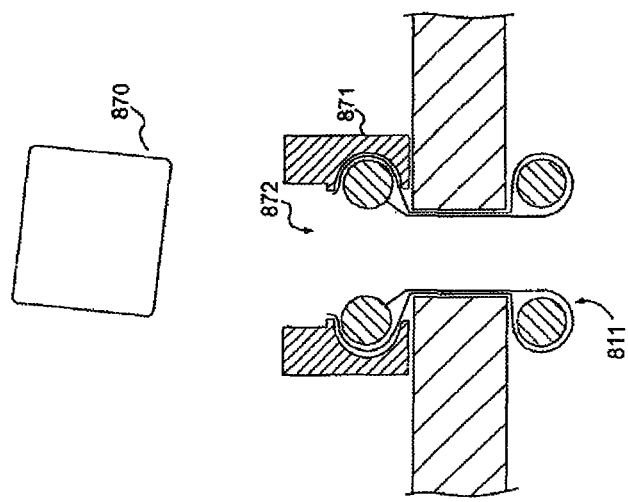
Figure 62:
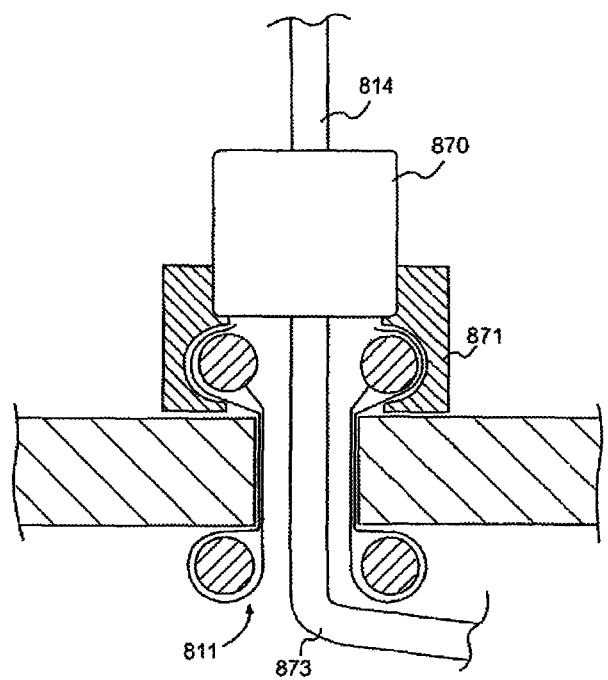
Figure 65:
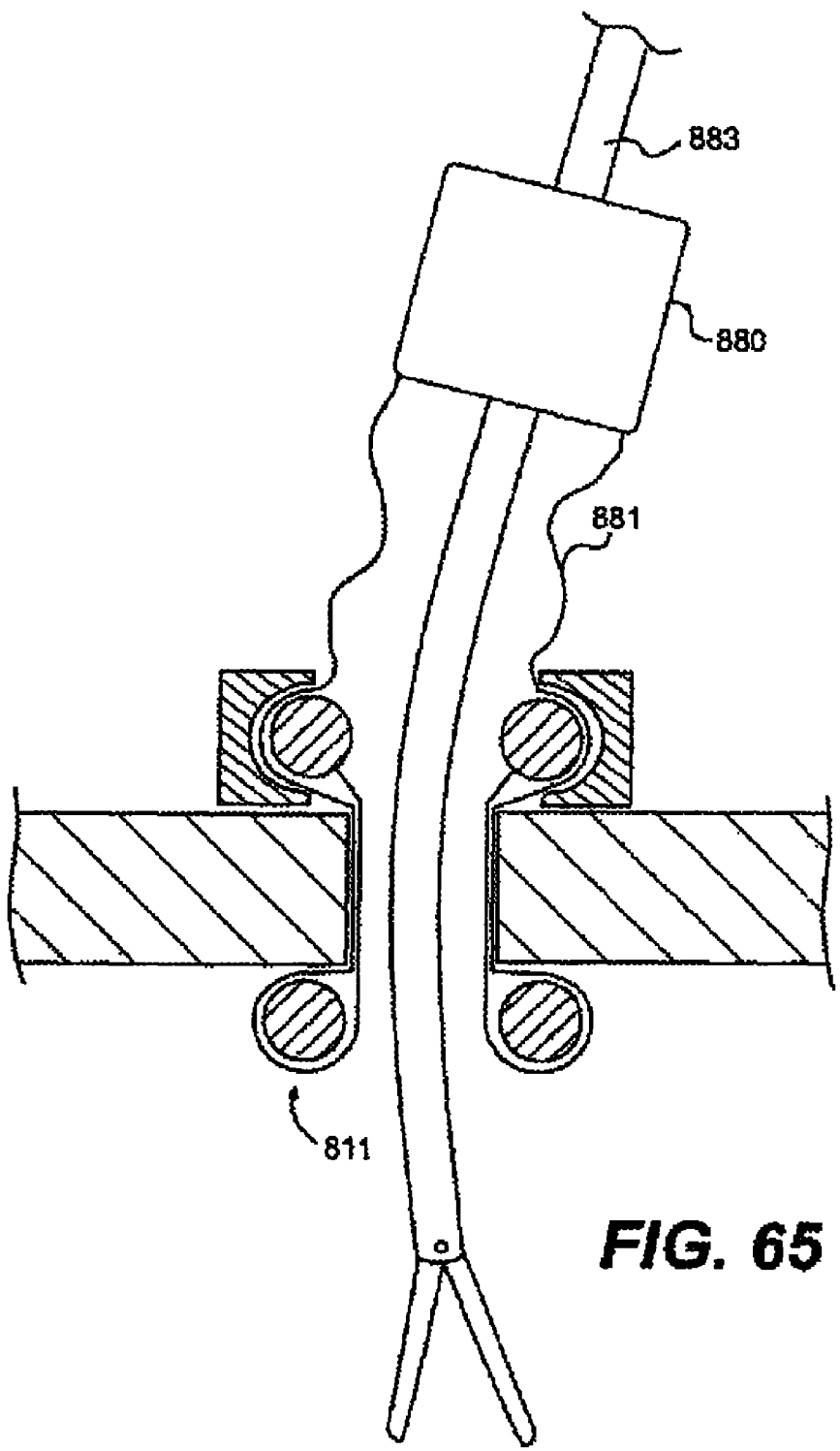
Figure 66:
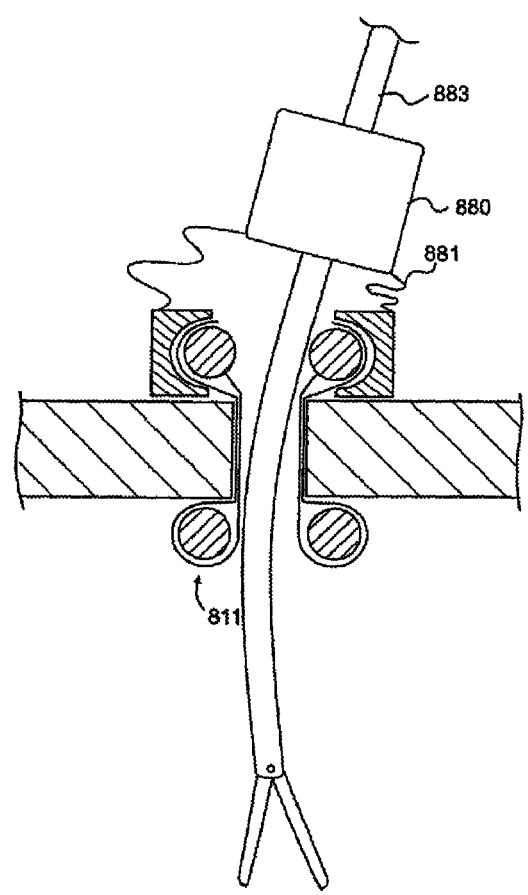

Referring now to FIGS. 60 to 62 another modular system is illustrated in which a valve 870 is releasably mounted to a retractor 811. The retractor 811 may have a proximal ring 871 with a recess 872 to receive the valve 870. An instrument shaft 814 can readily pass through the valve 870 and retractor 811. At least a section 873 of the shaft 814 can be bent or steered almost immediately distal of the retractor.

Referring now to FIGS. 63 to 66 any suitable valve 880 may be coupled to a retractor 811 using excess sleeve material 881 from the retractor 811. The valve 880 may be pulled upwardly to deploy the base retractor 811. The excess sleeve material 881 provides a flexible neck which facilitates easy introduction of objects such as an instrument 883, even one having a bent shaft (FIG. 119). As illustrated in FIG. 120 such an arrangement also facilitates additional instrument reach by allowing the valve 880 to be moved closer to the base retractor 811.

Figure 70:
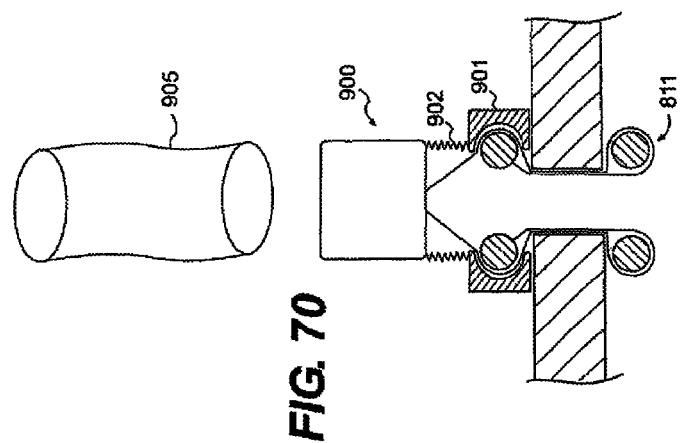
Figure 69:
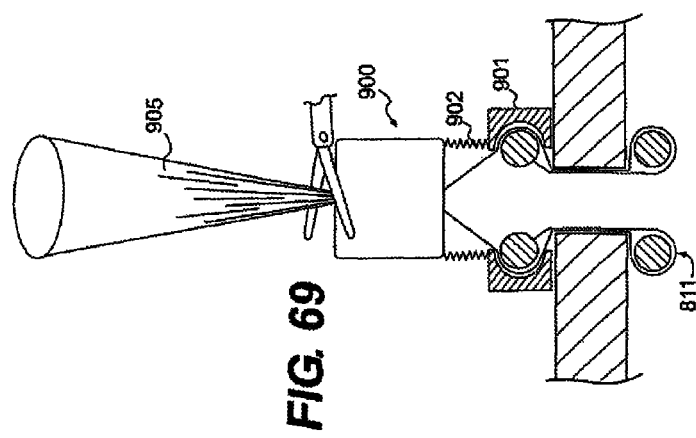

Referring to FIGS. 67 to 72 there is illustrated another access port comprising a wound protector and retractor device 811 and a valve 900. The valve 900 is connected to an outer guide ring 901 of the retractor device 811 by a sleeve 902 which in this case is of malleable material of corrugated configuration somewhat in the manner of the bendable hinge portion of a bendable drinking straw. The sleeve 902 may be pre-shaped to be offset from the longitudinal axis of the retractor to facilitate ease of insertion of an instrument or the like. The corrugated sleeve 902 may be compressed as illustrated in FIG. 68 to provide a low profile to facilitate outlining any of excess retractor sleeve as illustrated in FIGS. 69 and 70. Thereafter, the corrugated sleeve 902 can be extended/elongated and is readily manipulated into a desired configuration. Because the sleeve 902 is malleable it will retain a desired bent shape, even when the abdomen is pressurised. Any excess retractor sleeve material 905 may be cut-away as illustrated or used as described above.

In this context the term "malleable" is used to denote an element which is capable of being manipulated into a desired position and/or orientation, and which retains this manipulated position and/or orientation under the typical stresses and strains applied when used for an intended purpose with a patient, for example during partial insertion of a laparoscopic instrument.

The access ports of the invention can be used in a number of ways. In one method the retractor is used as described above, the distal inner ring being inserted into an incision, the outer ring being slid to controllably radially expand the incision. The retractor may then be locked in position. If necessary, the outer ring can be moved further downwardly to create a larger incision.

In some arrangements an instrument may be bent manually outside the body and the bent instrument is delivered through the access port to readily access the operative site.

In a further embodiment an instrument is inserted into the access port and the surgeon uses the abdominal wall itself to bend the instrument and then insert the bent section further into the abdomen.

In all cases the sleeve may be gripped by gripping a valve or other element mounted thereto.

The access ports of the invention have at least some of the following advantages:

Controlled Radial Expansion
  1. Greater access using smaller incision
  2. Can vary incision size as need be (e.g. specimen removal during lap coli.)

Greater Sealing Capabilities
  1. No gas leakage from the wound margins
  2. Cannot be inadvertently pulled out of the incision
  3. Will seal any incision and never require secondary sealing method (suture, Hasson port, etc.)

Eliminate Intra-Abdominal Profile
  1. Gives back more working space in the abdomen (critical in pelvic surgery)
  2. Perineal access for operations such as Radical Prostatectomy.

Protection of Wound from Infection and Cancer Seeding
  1. Tight seal with no "chimney stack" effect
  2. Upon removal all areas of potential contamination are isolated from the incision Reduced Extra-Abdominal Profile
  1. Will increase the effective working length of an instrument
  2. Greater working area outside the abdomen Increase the Freedom of Movement of Conventional Laparoscopic Instruments The invention is not limited to the embodiments hereinbefore described, with reference to the accompanying drawings, which may be varied in construction and detail.

The invention claimed is:

1. A surgical device, comprising:
  a wound retractor, including:
    a distal ring,
    a proximal ring, and
    a wound retracting sleeve extending at least between the distal ring and the proximal ring, wherein the wound retractor is for retracting a wound opening via shortening of an axial extent of the wound retracting sleeve that extends between the distal ring and the proximal ring; and
  a sealing assembly coupled to the wound retractor, the sealing assembly including:
    an annular base supporting at least a portion of the proximal ring, the annular base having a periphery,
    a flexible covering coupled to the periphery of the annular base, and
    a valve member coupled to the flexible covering, wherein the flexible covering and the valve member form a seal across the annular base and the proximal ring, and the valve member includes:
      a body, and
      an accessway surrounded by the body, wherein the accessway is sized to receive an instrument, and wherein a surface of the body that defines the accessway sealingly engages the instrument.

2. The surgical device of claim 1, wherein the flexible covering includes an opening, and the valve member forms a seal across the opening.

3. The surgical device of claim 1, wherein the valve member is movable in a proximal-distal direction relative to the annular base.

4. The surgical device of claim 1, wherein at least a portion of the valve member is movable towards and away from the periphery of the annular base.

5. The surgical device of claim 1, wherein the valve member directly contacts a proximalmost end of the flexible covering, and the annular base directly contacts a distalmost end of the flexible covering.

6. The surgical device of claim 1, wherein the wound retractor includes a central longitudinal axis, the accessway includes a central longitudinal axis, and the flexible covering facilitates tilting of the central longitudinal axis of the accessway relative to the central longitudinal axis of the wound retractor.

7. The surgical device of claim 1, wherein the annular base receives the proximal ring.

8. A surgical device, comprising:
  a wound retractor, including:
    a distal ring,
    a proximal ring, and a wound retracting sleeve extending at least between the distal ring and the proximal ring, wherein the wound retractor is for retracting a wound opening via shortening of an axial extent of the wound retracting sleeve that extends between the distal ring and the proximal ring; and a sealing assembly coupled to the wound retractor, the sealing assembly including:
a base, wherein at least a portion of the proximal ring and at least a portion of the wound retracting sleeve mount onto the annular base, with the portion of the wound retracting sleeve being held between the proximal ring and the base, and wherein the base includes a periphery,
a flexible covering coupled to the periphery of the base, and
a valve member coupled to the flexible covering, wherein the flexible covering and the valve member form a seal across the base and the proximal ring, and the valve member includes:
a body, and
an accessway surrounded by the body, wherein the accessway is sized to receive an instrument, and wherein a surface of the body that extends about the accessway sealingly engages the instrument.

9. The surgical device of claim 8, wherein the flexible covering is coupled to a proximalmost end of the periphery of the base.

10. The surgical device of claim 8, wherein the flexible covering includes an opening, and valve member forms a seal across the opening.

11. The surgical device of claim 8, wherein the valve member is pivotable relative to the base.

12. The surgical device of claim 8, wherein the valve member is movable in a proximal-distal direction relative to at least a portion of the flexible covering.

13. The surgical device of claim 8, wherein the valve member directly contacts a proximal portion of the flexible covering, and a distal portion of the flexible covering directly contacts the base.

14. A surgical device, comprising:
a wound retractor, including:
a distal ring,
a proximal ring, and
a wound retracting sleeve extending at least between the distal ring and the proximal ring, wherein the wound retractor is for retracting a wound opening via shortening of an axial extent of the wound retracting sleeve that extends between the distal ring and the proximal ring; and a sealing assembly coupled to the wound retractor, the sealing assembly including:
an annular base including a recess, wherein the proximal ring extends into the recess, and wherein the annular base has a periphery,
a flexible cover coupled to the periphery of the annular base and covering at least a portion of the annular base, wherein the flexible cover includes an opening formed therein, and
a valve member in the opening of the flexible cover, wherein the flexible cover and the valve member form a seal across the annular base and the proximal ring, and the valve member includes:
a body, and
an accessway surrounded by the body, wherein the accessway is sized to receive an instrument, and wherein a surface of the body that surrounds the accessway sealingly engages the instrument.

15. The surgical device of claim 14, wherein a distal portion of the flexible cover is coupled to a proximal portion of the periphery of the annular base.

16. The surgical device of claim 14, wherein the valve member forms a seal across the opening in the flexible cover.

17. The surgical device of claim 14, wherein the valve member is movable in proximal-distal direction relative to the annular base.

18. The surgical device of claim 14, wherein the annular base includes a central longitudinal axis, and at least a portion of the valve member is movable away from the central longitudinal axis.

19. The surgical device of claim 14, wherein the valve member directly contacts a proximal portion of the flexible cover, and a distal portion of the flexible cover directly contacts the annular base.

20. The surgical device of claim 14, wherein the annular base includes a central longitudinal axis, the accessway includes a central longitudinal axis, and the flexible cover facilitates tilting of the central longitudinal axis of the accessway relative to the central longitudinal axis of the annular base.

* * * * *